US008919039B2

(12) United States Patent
Huang et al.

(10) Patent No.: US 8,919,039 B2
(45) Date of Patent: Dec. 30, 2014

(54) METHODS AND COMPOSITIONS USING FUNGAL LACCASES TO REDUCE TURF THATCH

(75) Inventors: Qingguo Huang, Fayetteville, GA (US); Sudeep S. Sidhu, Griffin, GA (US); Paul L. Raymer, Milner, GA (US); Robert N. Carrow, Griffin, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 652 days.

(21) Appl. No.: 13/249,729

(22) Filed: Sep. 30, 2011

(65) Prior Publication Data

US 2012/0079764 A1  Apr. 5, 2012

Related U.S. Application Data

(60) Provisional application No. 61/388,160, filed on Sep. 30, 2010.

(51) Int. Cl.
*A01G 1/00* (2006.01)
*C12N 9/02* (2006.01)

(52) U.S. Cl.
CPC ....... *C12N 9/0061* (2013.01); *C12Y 110/03002* (2013.01)
USPC .................................................. 47/58.1 R

(58) Field of Classification Search
USPC ....................... 47/58.1 R, 1.01 R, 1.01 F, 1.43
See application file for complete search history.

(56) References Cited

U.S. PATENT DOCUMENTS

| | | | |
|---|---|---|---|
| 6,506,956 B1 * | 1/2003 | Yuki et al. | 435/262.5 |
| 2008/0248016 A1 * | 10/2008 | Paloheimo et al. | 424/94.4 |
| 2009/0311752 A1 * | 12/2009 | Bodie et al. | 435/72 |

OTHER PUBLICATIONS

Anatai, Sylvester P., and Crawford, Don L., Degradation of Extractive-free Lignocelluloses by Coriulus versicolor and Proia placenta, European J. Appl. Microbiol Biotechnol (1982) 14:165-168.
Sartain, J.B., and Volk, B.G., Influence of Selected White-Rot Fungi and Topdressings on the Composition of Thatch components of Four Turfgrasses, Agronomy Journal, vol. 76, (May-Jun. 1984), 359-362.
Martin, S.B., and Dale, J.L., Biodegradation of Turf Thatch With Wood-Decay Fungi, Photopathology (1980) 70:297-301.
Xu, Jie and Yang, Qian, Isolation and Characterization of Rice Straw Degrading, Streptomyces griseorubens C-5, Biodegradation (2010) 21:107-116.
Unpublished, internal progress report from inventor, Dr. Qingguo Huan to research sponsor, the Golf Course Superintendents Association of America (GCSAA) on A Novel Method to Facilitate Biodethatching Using Fungal Laccases, Oct. 31, 2008.
Unpublished, internal progress report from inventor, Dr. Qingguo Huan to research sponsor, the Golf Course Superintendents Association of America (GCSAA) on A Novel Method to Facilitate Biodethatching Using Fungal Laccases, May 16, 2009.
Ohkuma, Moriya et al., Lignin degradation and roles of white rot fungi: Study on an efficient symbiotic system in fungus-growing termites and its application to bioremediation, RIKEN Review No. 42 (Dec. 2001).

(Continued)

*Primary Examiner* — Monica Williams
(74) *Attorney, Agent, or Firm* — Thomas|Horstemeyer, LLP

(57) ABSTRACT

The present disclosure describes methods and compositions for reducing turf thatch and/or preventing turf thatch buildup.

18 Claims, 14 Drawing Sheets

(56) References Cited

OTHER PUBLICATIONS

Chamberlain, K., Crawford, D.L., Thatch biodegradation and antifungal activities of two lignocellulolytic Streptomyces strains in laboratory cultures and in golf green turfgrass, Can J Microbiol 2000; 46:550-8.

Research agreement between The University of Georgia Research Foundation and The Environmental Institute for Golf, effective May 8, 2008.

* cited by examiner

FIGURE 16

Tables from Example 2:
Table 1. Analysis of variance (ANOVA) table

| Source of Variation | df | Organic layer thickness (OLT) | Total organic carbon (TOC) (0-5.0 cm) | Acid-soluble lignin (ASL) | Acid-insoluble lignin (AIL) | Thatch layer thickness (TLT) | Mat layer thickness (MLT) | Total organic carbon (TOC) (0-2.5 cm) | Total organic carbon (TOC) (2.5 – 5.0 cm) | Saturated hydraulic conductivity (SHC) |
|---|---|---|---|---|---|---|---|---|---|---|
| | | cm | % | % | % | cm | cm | % | % | cm h$^{-1}$ |
| | | | | | Mean Square Values | | | | | |
| Effects | | | | | | | | | | |
| Full Model | | | | | | | | | | |
| Time | 1 | 36.49*** | 20.08*** | 0.5582*** | 1.026 | | | | | |
| Laccase | 2 | 0.9921*** | 1.050*** | 0.5558*** | 4.765*** | | | | | |
| Guaiacol | 1 | 0.0969 | 0.0103 | 0.0986 | 0.5073 | | | | | |
| Time*laccase | 2 | 1.092*** | 0.6082*** | 0.2295** | 0.8449 | | | | | |
| Time*guaiacol | 1 | 0.1369 | 0.0446 | 0.1960 | 0.7611 | | | | | |
| Error | 4 2 | 0.0771 | 0.0583 | 0.0282 | 0.3022 | | | | | |
| 2 Months | | | | | | | | | | |
| Rep | 4 | 0.0184 | 0.1694 | 0.0383* | 0.1068 | | | | | |
| Laccase | 3 | 0.2083 | 0.1671 | 0.5018*** | 7.605*** | | | | | |
| Guaiacol | 1 | 0.0070 | 0.0184 | 0.0000028 | 0.00010 | | | | | |
| Laccase*guaiacol | 3 | 0.0385 | 0.3759 | 0.0153 | 0.0302 | | | | | |
| Error | 2 8 | 0.08082 | 0.07609 | 0.009634 | 0.3230 | | | | | |
| 9 Months | | | | | | | | | | |
| Rep | 3 | 0.1014 | 0.04630 | 0.07850 | 1.203*** | 0.0739 | 0.0168 | 1.945 | 0.0614 | 3.239 |
| Laccase | 2 | 1.921*** | 1.4398*** | 0.6669*** | 4.301*** | 0.9602*** | 0.1653 | 16.60*** | 0.2741 | 451.9*** |
| Guaiacol | 1 | 0.2193 | 0.0440 | 0.2577* | 1.1301 | 0.0453 | 0.0652 | 1.922 | 0.0405 | 193.9*** |
| Laccase*guaiacol | 2 | 0.0355 | 0.02990 | 0.05800 | 0.3554 | 0.0135 | 0.0879 | 1.538 | 0.0104 | 140.7*** |
| Error | 1 5 | 0.0872 | 0.0813 | 0.0407 | 0.1319 | 0.0403 | 0.1123 | 1.0030 | 0.0827 | 3.443 |

\* Significant at the 0.05 probability level   \*\*Significant at the 0.01 probability level   \*\*\* Significant at the 0.001 probability level

FIGURE 17

Table 2. Organic layer thickness (OLT), total organic carbon (TOC) content (0-5.0 cm depth) for different treatments used on a creeping bentgrass after two and nine months of treatment application.

| Treatment | Organic layer thickness | | Total organic carbon (0-5.0) | |
|---|---|---|---|---|
| | cm | | % | |
| Laccase activity units cm$^{-2}$ area | 2 Months | 9 Months | 2 Months | 9 Months |
| 0 (Control) | 4.84$^a$ | 6.93$^a$ | 3.37$^{ab}$ | 4.95$^a$ |
| 0+G† | 4.74$^{ab}$ | 6.82$^{ab}$ | 3.44$^{ab}$ | 4.73$^a$ |
| 0.206 | 4.57$^{ab}$ | 6.73$^{ab}$ | 3.64$^a$ | 5.00$^a$ |
| 0.206+G | 4.76$^{ab}$ | 6.38$^{bc}$ | 3.43$^{ab}$ | 4.94$^a$ |
| 2.06 | 4.81$^a$ | 5.98$^{cd}$ | 3.27$^b$ | 4.17$^b$ |
| 2.06+G | 4.77$^{ab}$ | 5.85$^d$ | 3.50$^{ab}$ | 4.19$^b$ |
| 20.6 | 4.42$^b$ | - | 3.63$^a$ | - |
| 20.6+G | 4.51$^{ab}$ | - | 3.39$^{ab}$ | - |

Values within a column bearing the same superscript are not significantly different †G: Guaiacol, acts as a mediator

FIGURE 18

Table 3. Extractive-free acid-soluble (ASL), acid-insoluble (AIL), and total lignin (TL) content for different treatments used on creeping bentgrass after two and nine months of treatment application.

| Treatment | Acid-soluble lignin | | Acid-insoluble lignin | | Total lignin | |
|---|---|---|---|---|---|---|
| Laccase activity units cm$^{-2}$ area | % | | % | | % | |
| | 2 Months | 9 Months | 2 Months | 9 Months | 2 Months | 9 Months |
| 0 (Control) | 4.37$^{ab}$ | 4.22$^{b}$ | 25.99$^{a}$ | 25.74$^{b}$ | 30.35$^{ab}$ | 29.97$^{b}$ |
| 0+G† | 4.38$^{ab}$ | 4.58$^{a}$ | 26.01$^{a}$ | 26.48$^{a}$ | 30.39$^{a}$ | 31.06$^{a}$ |
| 0.206 | 4.41$^{a}$ | 4.14$^{b}$ | 25.69$^{a}$ | 25.45$^{bc}$ | 30.10$^{ab}$ | 29.59$^{b}$ |
| 0.206+G | 4.33$^{abc}$ | 4.14$^{b}$ | 25.54$^{a}$ | 25.39$^{bc}$ | 29.88$^{ab}$ | 29.55$^{b}$ |
| 2.06 | 4.27$^{bc}$ | 3.71$^{c}$ | 25.40$^{a}$ | 24.34$^{d}$ | 29.67$^{ab}$ | 28.04$^{d}$ |
| 2.06+G | 4.23$^{c}$ | 3.95$^{bc}$ | 25.39$^{a}$ | 24.96$^{c}$ | 29.62$^{b}$ | 28.90$^{c}$ |
| 20.6 | 3.85$^{d}$ | - | 23.94$^{b}$ | - | 27.79$^{c}$ | - |
| 20.6+G | 3.95$^{d}$ | - | 24.10$^{b}$ | - | 28.01$^{c}$ | - |

Values within a column bearing the same superscript are not significantly different †G: Guaiacol, acts as a mediator

FIGURE 19

Table 4. Effect of different treatments on the visual quality ratings on creeping bentgrass.

| Treatments | Weeks | | | | | | | | | | | | |
|---|---|---|---|---|---|---|---|---|---|---|---|---|---|
| Laccase activity units cm$^{-2}$ area | 2 | 4 | 6 | 8 | 10 | 12 | 32 | 34 | 36 | 38 | Early | Late | All |
| 0 | 7.05$^{ab}$ | 6.74$^a$ | 8.32$^{ab}$ | 7.75$^a$ | 7.20$^a$ | 8.00$^{ab}$ | 7.88$^a$ | 7.89$^a$ | 8.29$^a$ | 8.49$^a$ | 7.47$^a$ | 7.96$^a$ | 7.75$^a$ |
| 0+G† | 7.02$^{ab}$ | 6.87$^a$ | 8.12$^{ab}$ | 7.73$^a$ | 7.14$^a$ | 8.07$^a$ | 7.77$^a$ | 7.74$^a$ | 8.06$^a$ | 8.39$^a$ | 7.44$^a$ | 7.86$^a$ | 7.55$^a$ |
| 0.206 | 7.19$^a$ | 6.75$^a$ | 8.16$^{ab}$ | 7.60$^a$ | 7.13$^a$ | 7.90$^{ab}$ | 8.01$^a$ | 8.00$^a$ | 8.14$^a$ | 8.40$^a$ | 7.43$^a$ | 7.80$^a$ | 7.75$^a$ |
| 0.206+G | 7.03$^a$ | 6.67$^a$ | 7.97$^b$ | 7.75$^a$ | 7.31$^a$ | 7.77$^b$ | 7.74$^a$ | 7.63$^a$ | 8.31$^a$ | 8.26$^{ab}$ | 7.36$^a$ | 7.84$^a$ | 7.46$^a$ |
| 2.06 | 7.19$^a$ | 7.04$^a$ | 8.31$^{ab}$ | 7.77$^a$ | 7.37$^a$ | 7.94$^{ab}$ | 7.89$^a$ | 7.94$^a$ | 8.11$^a$ | 8.13$^b$ | 7.58$^a$ | 7.90$^a$ | 7.60$^a$ |
| 2.06+G | 6.88$^{ab}$ | 6.73$^a$ | 8.39$^a$ | 7.76$^a$ | 7.27$^a$ | 7.74$^b$ | 7.87$^a$ | 8.00$^a$ | 8.21$^a$ | 8.39$^a$ | 7.44$^a$ | 7.91$^a$ | 7.60$^a$ |
| 20.6 | 6.70$^b$ | 6.86$^a$ | 8.42$^a$ | 7.80$^a$ | - | - | - | - | - | - | 7.49$^a$ | - | - |
| 20.6+G | 6.86$^{ab}$ | 6.72$^a$ | 8.18$^{ab}$ | 7.90$^a$ | - | - | - | - | - | - | 7.46$^a$ | - | - |

Values within a column bearing the same superscript are not significantly different.

†G:Guaiacol, acts as a mediator

FIGURE 20

Table 5. Grass index values for different treatments on creeping bentgrass.

| Treatments | Weeks | | | | | | | | | | | | |
|---|---|---|---|---|---|---|---|---|---|---|---|---|---|
| Laccase activity units cm$^{-2}$ area | 2 | 4 | 6 | 8 | 10 | 12 | 32 | 34 | 36 | 38 | Early | Late | All |
| 0 | 7.03$^{ab}$ | 6.47$^a$ | 7.47$^a$ | 6.71$^a$ | 7.70$^a$ | 8.17$^{ab}$ | 8.15$^a$ | 8.23$^a$ | 9.14$^a$ | 9.34$^a$ | 6.92$^a$ | 8.46$^a$ | 7.84$^a$ |
| 0+G† | 7.11$^{ab}$ | 6.45$^a$ | 6.96$^{ab}$ | 6.53$^a$ | 7.94$^a$ | 8.31$^a$ | 8.20$^a$ | 8.47$^a$ | 9.04$^a$ | 9.06$^a$ | 6.76$^a$ | 8.50$^a$ | 7.81$^a$ |
| 0.206 | 7.21$^a$ | 6.40$^{ab}$ | 7.11$^{ab}$ | 6.55$^a$ | 7.70$^a$ | 7.96$^{ab}$ | 8.22$^a$ | 7.93$^a$ | 9.07$^a$ | 9.10$^a$ | 6.82$^a$ | 8.33$^a$ | 7.73$^a$ |
| 0.206+G | 7.15$^{ab}$ | 6.33$^{ab}$ | 6.90$^{ab}$ | 6.53$^a$ | 7.61$^a$ | 7.84$^b$ | 8.36$^a$ | 8.10$^a$ | 9.06$^a$ | 9.34$^a$ | 6.73$^a$ | 8.39$^a$ | 7.72$^a$ |
| 2.06 | 7.10$^{ab}$ | 6.44$^a$ | 7.27$^{ab}$ | 6.53$^a$ | 7.66$^a$ | 8.14$^{ab}$ | 8.10$^a$ | 8.29$^a$ | 9.07$^a$ | 9.33$^a$ | 6.84$^a$ | 8.43$^a$ | 7.79$^a$ |
| 2.06+G | 6.94$^{ab}$ | 6.19$^{ab}$ | 7.50$^a$ | 6.49$^a$ | 7.84$^a$ | 8.20$^{ab}$ | 8.16$^a$ | 8.10$^a$ | 9.20$^a$ | 9.12$^a$ | 6.78$^a$ | 8.43$^a$ | 7.77$^a$ |
| 20.6 | 6.68$^b$ | 6.02$^b$ | 6.70$^b$ | 6.72$^a$ | - | - | - | - | - | - | 6.53$^b$ | - | - |
| 20.6+G | 6.92$^{ab}$ | 6.16$^{ab}$ | 6.96$^{ab}$ | 6.74$^a$ | - | - | - | - | - | - | 6.73$^a$ | - | - |

Values within a column bearing the same superscript are not significantly different.

†G:Guaiacol, acts as a mediator

METHODS AND COMPOSITIONS USING FUNGAL LACCASES TO REDUCE TURF THATCH

CROSS-REFERENCE TO RELATED APPLICATION

This application claims priority to copending U.S. provisional application entitled, "Methods and Compositions using Fungal Laccases to Reduce Turf Thatch," having Ser. No. 61/388,160, filed Sep. 30, 2010, which is entirely incorporated herein by reference.

BACKGROUND

Thatch, a layer of organic matter including tightly intermingled dead and living leaves, stems, and roots, often develops between the soil surface and the green vegetation and, left untreated, can result in deterioration of the turf quality. Thatch includes stolons, rhizomes, roots, crown tissue, leaf sheaths and blades. Thatch layer intermixed with sand or soil is known as mat layer. The mat layer generally lies below the thatch layer where sand or soil is intermingled with thatch due to cultural practices like core aeration and top dressing.

High organic matter accumulation in the form of thatch or mat causes depletion of oxygen and decreased saturated hydraulic conductivity and increased water content. This makes the turf more susceptible to drought, cold, insects, diseases and other problems such as welt wilt, soft surface, black layer, limited rooting etc. Thatch control thus represents a challenge in turf management.

Management of turfgrass greens includes monitoring and control of the formation of thatch and mat layers. A cause of problems in the thatch-mat layer includes the rapid change in the nature of organic matter from the structured organic matter in live plant root tissues to the unstructured organic matter in dead plant tissues. Although live organic matter is not supposed to adversely affect soil's physical properties, the dead gelatinous organic matter in thatch swells in the presence of water during decomposition and plugs the soil macropores (air-filled pores), causing low oxygen levels in the root zones.

Extensive root death during persistent wet and hot conditions plugs the air-filled pores causing a decrease in the infiltration rate as well as oxygen stress. Increased accumulation of organic matter causes anaerobic conditions, which further slows the rate of organic matter decomposition. Grasses generally produce more adventitious roots (surface roots) during anaerobic conditions, further increasing organic matter content. Although a small amount of organic matter reduces surface hardness, moderates soil temperature extremes, increases the resilience and improves wear tolerance of turfgrass surface, excessive thatch and mat layers are undesirable in turfgrass. Unfortunately, control and management of thatch and mat layer buildup poses a challenge.

Cultural or mechanical practices like core-aeration, vertical mowing, grooming, and application of topdressing (such as sand) have been used to manage the thatch-mat buildup but have not proven sufficiently effective. These cultural practices are also intensive in terms of cost, energy, and labor, and some may cause adverse effects on turfgrass quality and site-use for a period of time.

Thatch-mat layer results due to a more rapid rate of organic matter accumulation than degradation. It is believed that the rate of thatch degradation, and most microbial degradation mechanisms, are restricted by the presence of lignin, a plant cell wall constituent that is resistant to microbial degradation. Lignin is a 3-dimensional amorphous polymer with a random and unorganized methoxylated phenyl propane structure that serves as a barrier in the cell walls to limit the accessibility to the more biodegradable plant materials, such as cellulose and hemicelluloses, by microbial degraders. Natural degradation of lignin is carried out in the environment by certain white-rot fungi which solubilize and mineralize lignin with the help of lignolytic enzymes thus exposing cellulosic materials for further bacterial degradation in the environment.

White rot fungi are recognized as one of the few active lignin degrading microorganisms found in the nature. Oxidative enzymes produced by fungi are able to attack the aromatic contents in lignin and produce free radicals, leading to degradation of lignin. White-rot fungi preferentially attack lignin over cellulose or hemicellulose in the wood tissue. This process of selective delignification exposes cellulosic materials for further bacterial degradation in the environment. Thatch is high in lignin, and, for this reason, turfgrass species high in lignin content are more resistant to decomposition.

Oxidative enzymes such as laccases, lignin peroxidases and manganese peroxidases produced by white rot fungi attack the aromatic components of lignin and contribute to its effective degradation. They have been used in the pulp and paper industry to remove lignin from wood pulp. Laccases, the multi copper oxidases, act on a wide variety of aromatic compounds by reducing oxygen to water.

SUMMARY

Briefly described, embodiments of the present disclosure provide for methods and compositions for reducing turf thatch.

Embodiments of methods of degrading turf thatch of the present disclosure include contacting the turf thatch with a composition including an isolated fungal laccase enzyme.

Embodiments of composition of the present disclosure for reducing turf thatch include formulations adapted for application to turfgrass where the formulations include an isolated fungal laccase enzyme. In embodiments, the formulation also includes water.

Embodiments of the present disclosure also include compositions for reducing turf thatch that include a particulate topdressing having isolated fungal laccase enzymes immobilized to the particles of the topdressing.

In embodiments of the methods and compositions of the present disclosure, the isolated laccase enzyme is from white rot fungi. In embodiments, the laccase enzyme is isolated from white rot fungi, such as, but not limited to *Trametes versicolor*.

Other systems, methods, features, and advantages of the present disclosure will be or become apparent to one with skill in the art upon examination of the following drawings and detailed description. It is intended that all such additional systems, methods, features, and advantages be included within this description, and be within the scope of the present disclosure.

BRIEF DESCRIPTION OF THE DRAWINGS

The disclosure can be better understood with reference to the following drawings, which are described in the description and examples below. The components in the drawings are not necessarily to scale, emphasis instead being placed upon clearly illustrating the principles of the present disclosure.

Extractive-free acid-insoluble lignin (AIL %) and Total Lignin % corresponds to the Y axis on the left and extractive-free acid-soluble lignin (ASL %) to the axis on the right.

Figure 2:
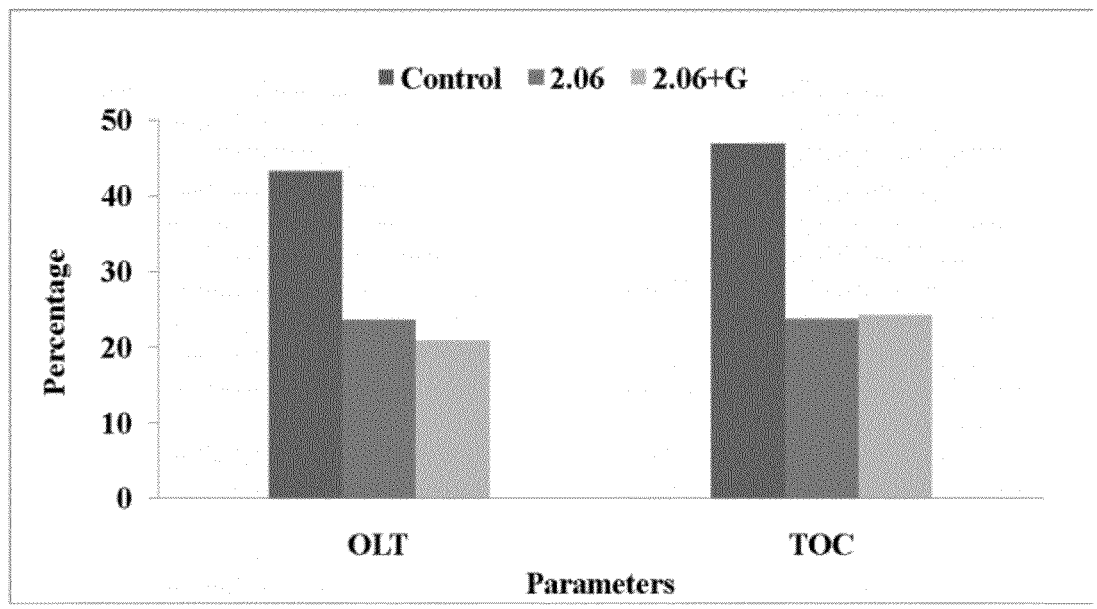

FIG. 2 is a bar graph illustrating organic layer thickness (OLT) and total organic carbon (TOC) (0-5.0 cm) percent increase within two sampling dates (2 and 9 months) in the greenhouse study on creeping bentgrass comparing control and laccase activity level of 2.06 units $cm^{-2}$ area with and without guaiacol (G).

Figure 3:
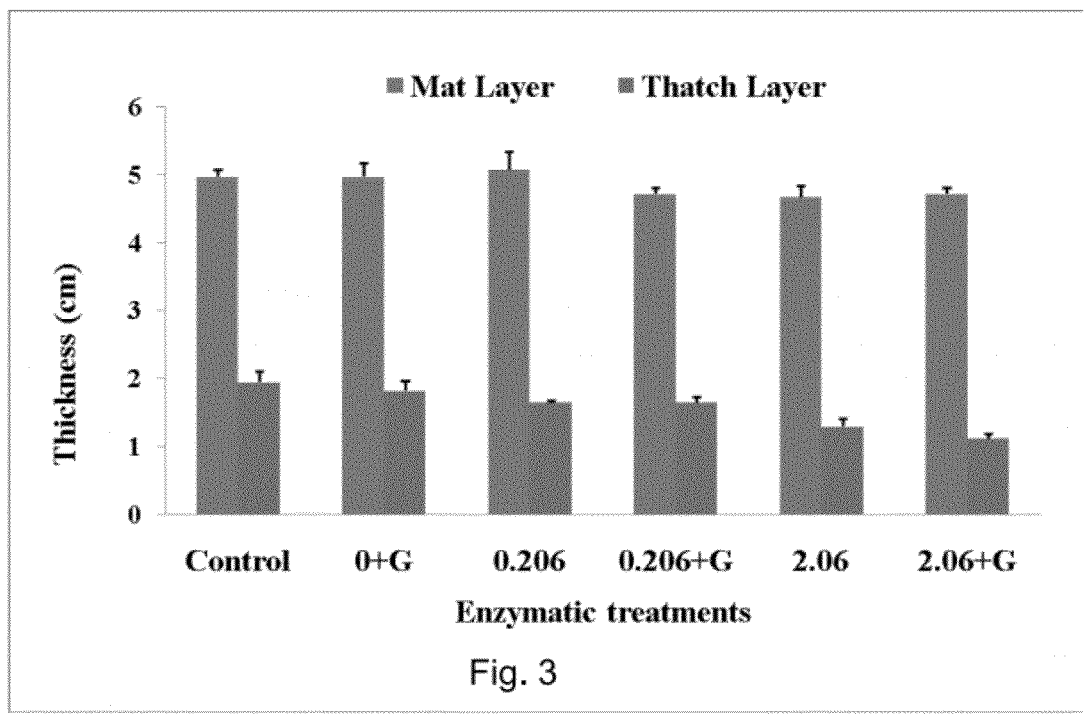

FIG. 3 is a bar graph illustrating thatch (TLT) and mat layer thickness (MLT) after nine months of treatment on creeping bentgrass in the greenhouse study with three different levels of laccase (0 (control), 0.206 and 2.06 units $cm^{-2}$ area) with and without the mediator, guaiacol (G). Values are means of four replicates, and error bars are standard errors. LSD for comparing the values within different treatments is 0.30 and 0.51 for thatch and mat layer thickness, respectively.

Figure 4:
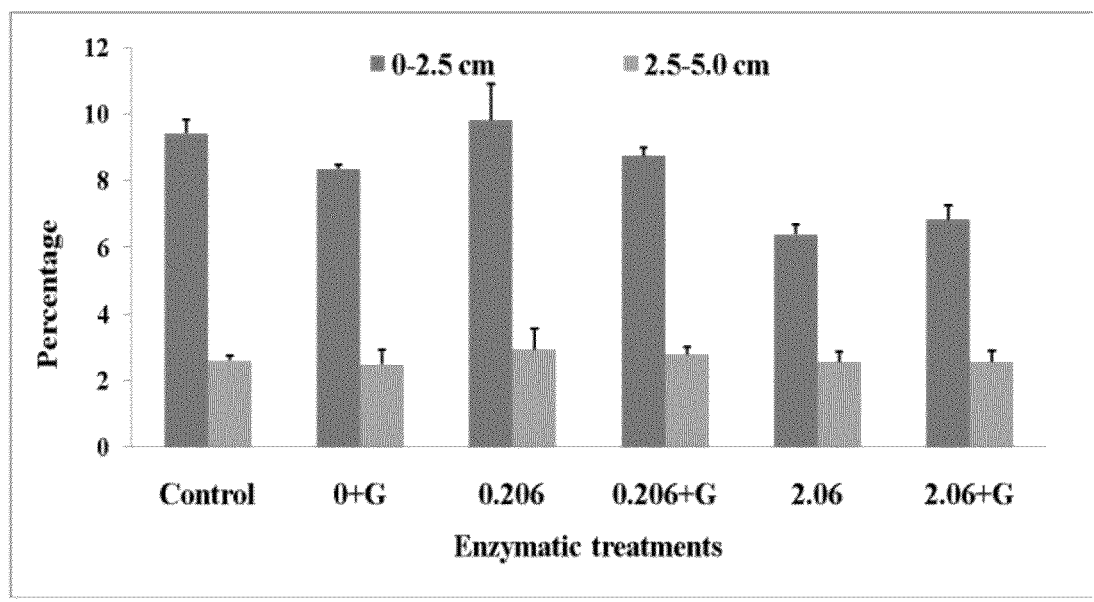

FIG. 4 is a bar graph illustrating total organic carbon (TOC) for 0-2.5 cm depth and 2.5 to 5.0 cm depth after nine months of treatment on creeping bentgrass in the greenhouse study with three different levels of laccase (0 (control), 0.206 and 2.06 units $cm^{-2}$) with and without the mediator, guaiacol (G). Values are means of four replicates, and error bars are standard errors. LSD for comparing the values within different treatments is 1.51 and 0.43 for 0-2.5 cm and 2.5-5.0 cm depth, respectively.

Figure 5:
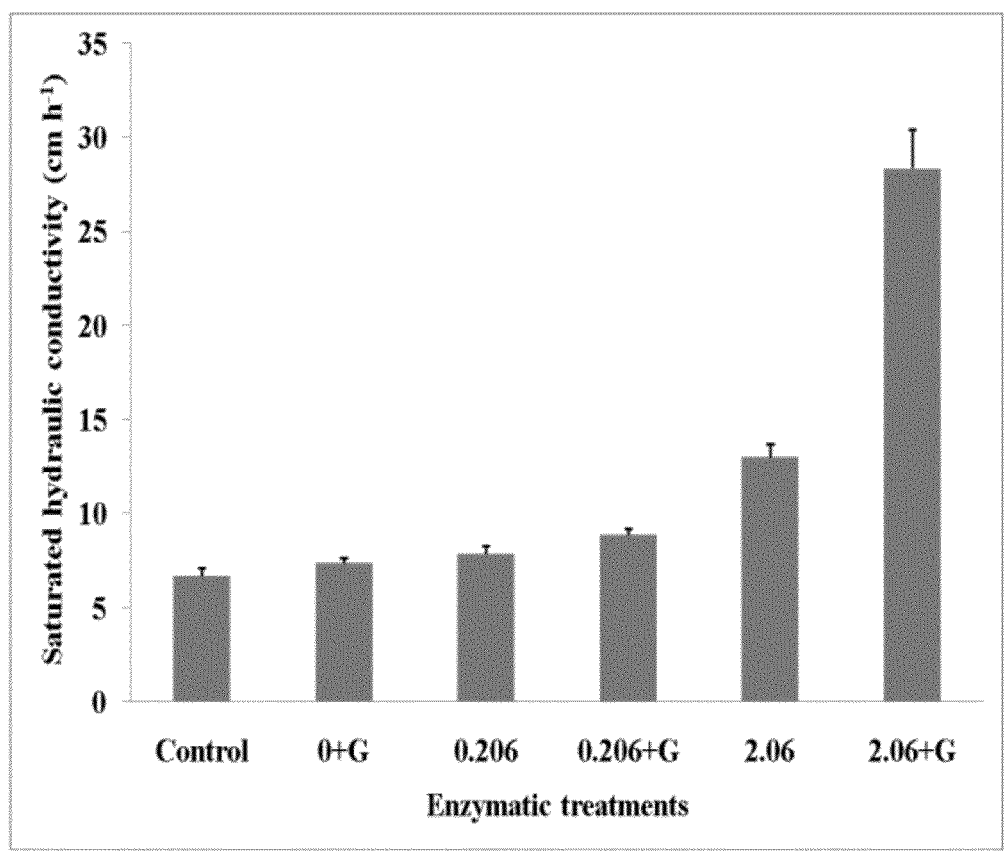

FIG. 5 is a bar graph illustrating saturated hydraulic conductivity (SHC) after nine months of treatment on creeping bentgrass in the greenhouse study with three different levels of laccase (0 (control), 0.206 and 2.06 units $cm^{-2}$) with and without the mediator, guaiacol (G). Values are means of four replicates, and error bars are standard errors. LSD for comparing the values within different treatments is 2.80.

Figure 6:
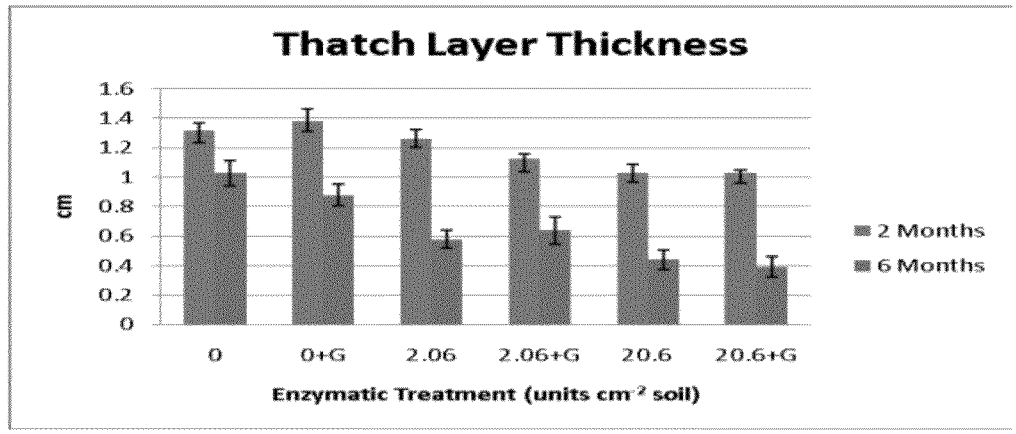

FIG. 6 is a bar graph illustrating thatch layer thickness (TLT) on dead bentgrass pots after two and six months of treatment with three different levels of laccase (0 (control), 2.06 and 20.6 units $cm^{-2}$, with and without the mediator, guaiacol (G).

Figure 7:
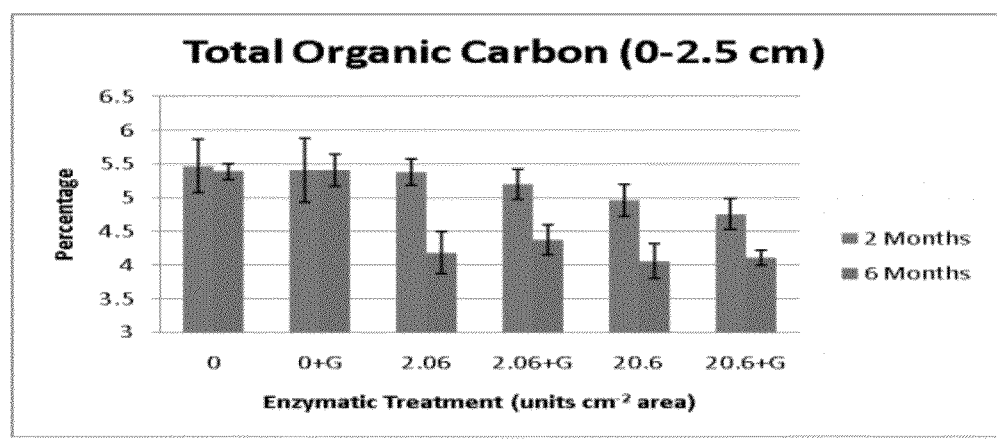

FIG. 7 is a bar graph illustrating total organic carbon (TOC) on dead bentgrass pots after two and six months of treatment with three different levels of laccase (0 (control), 2.06 and 20.6 units $cm^{-2}$, with and without the mediator, guaiacol (G).

Figure 8:
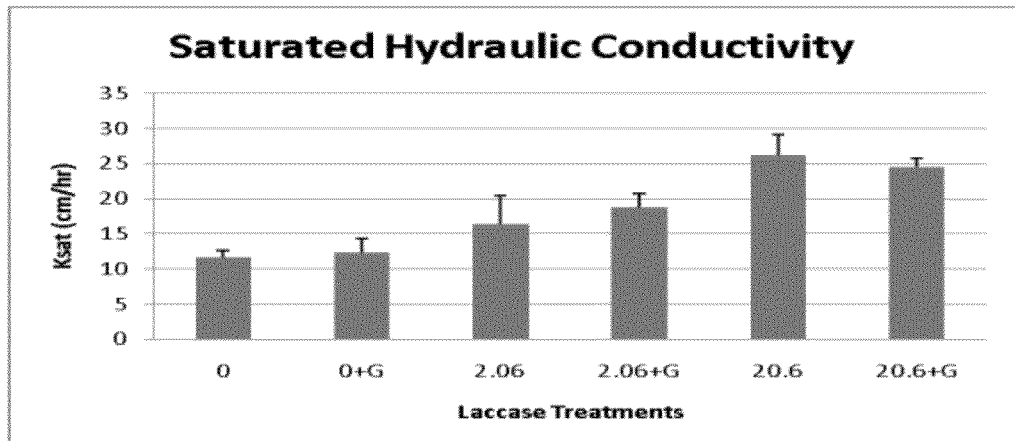

FIG. 8 is a bar graph illustrating saturated hydraulic conductivity (SHC) on dead bentgrass pots after two months of treatment application with three different levels of laccase (0 (control), 2.06 and 20.6 units $cm^{-2}$, with and without the mediator, guaiacol (G).

Figure 9:
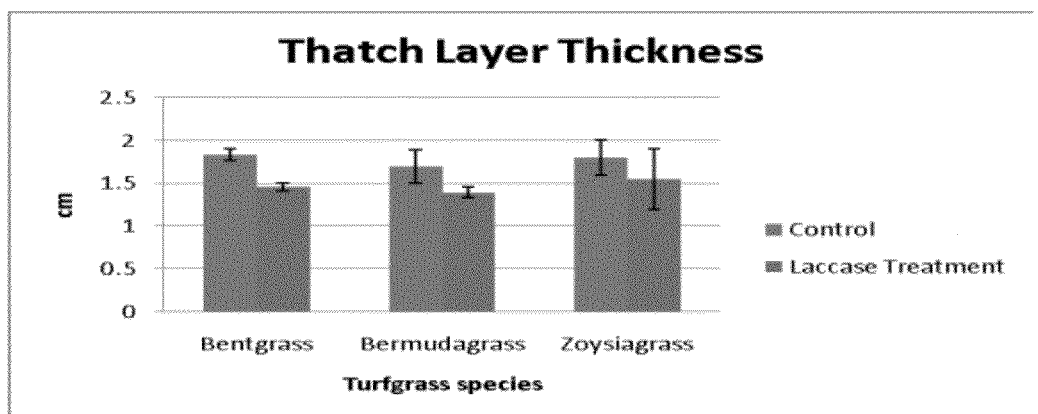

FIG. 9 is a bar graph illustrating thatch layer thickness after seven months of laccase application in the field study on bentgrass, bermudagrass, and zoysiagrass. Laccase was applied every two weeks at 2.06 units $cm^{-2}$.

Figure 10:
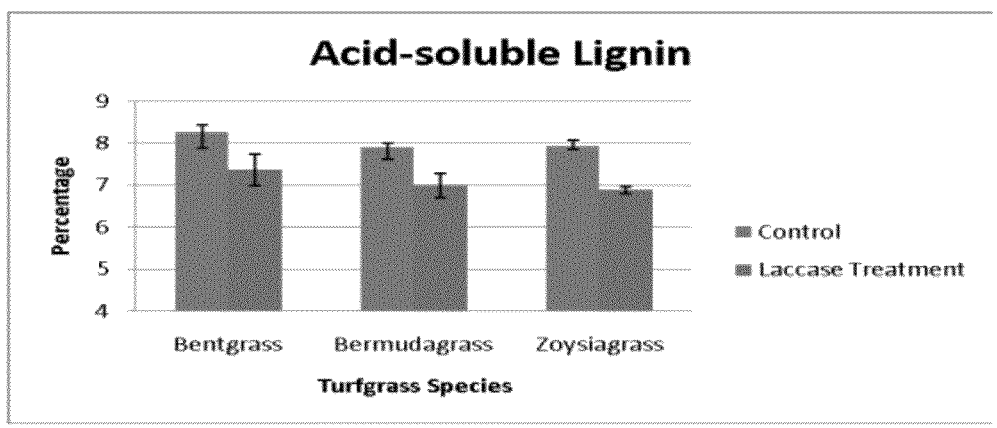

FIG. 10 is a bar graph illustrating extractive-free acid-soluble lignin after seven months of laccase application in the field study on bentgrass, bermudagrass, and zoysiagrass thatch layer. Laccase was applied every two weeks at 2.06 units $cm^{-2}$.

Figure 11:
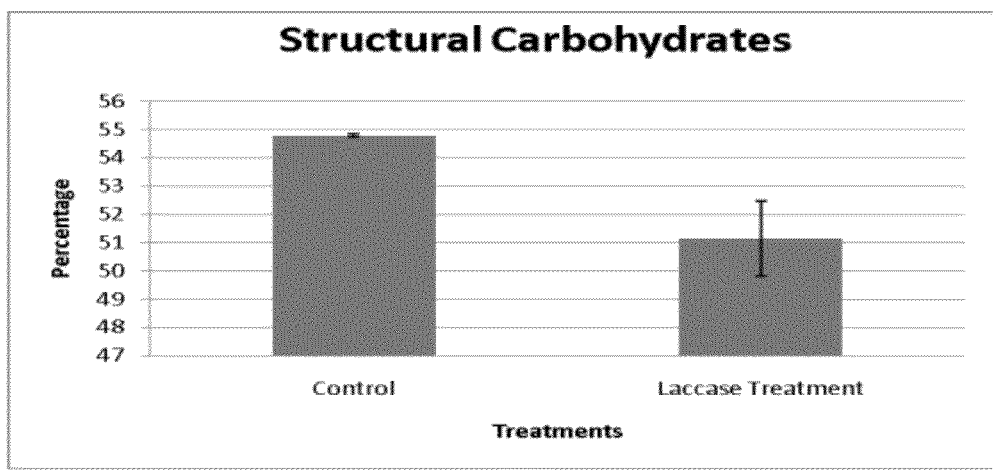

FIG. 11 is a bar graph illustrating the percentage of structural carbohydrates (cellulosic and hemicellulosic sugars) in bentgrass thatch layer after seven months of laccase application in the field study. Laccase was applied every two weeks at 2.06 units $cm^{-2}$.

Figure 12:
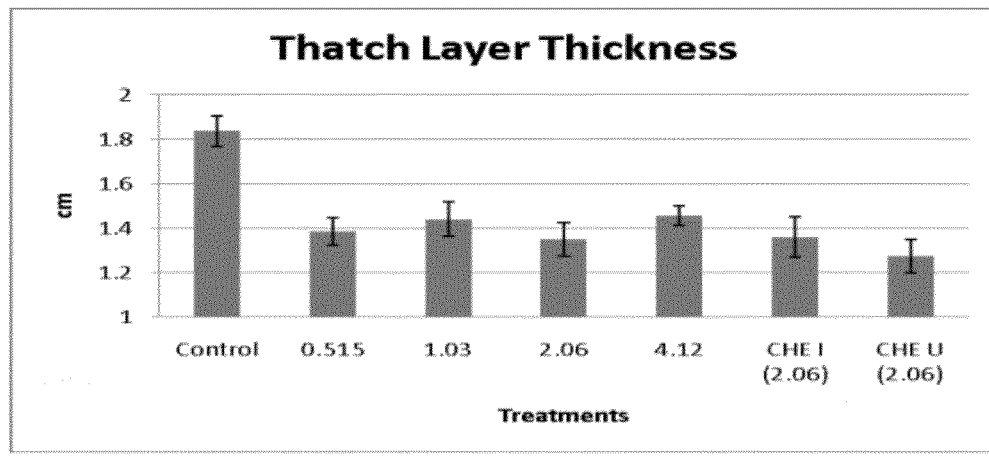
Figure 13:
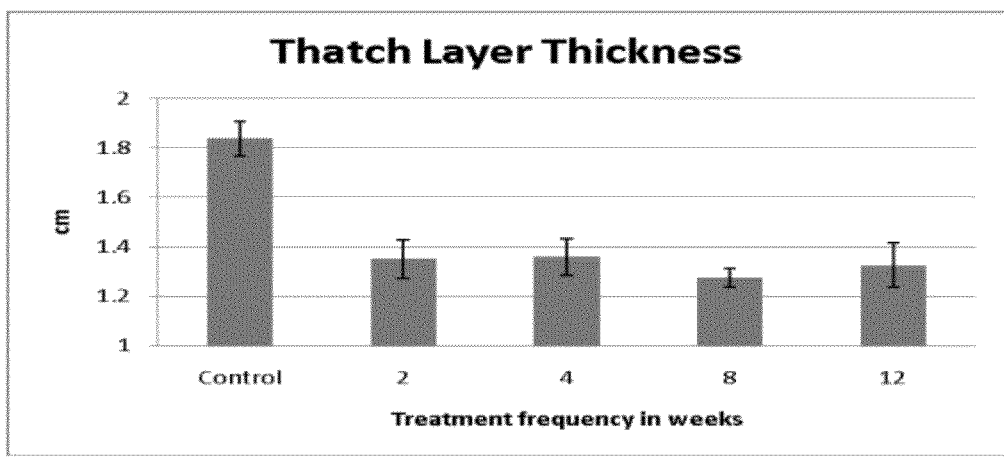

FIG. 12 is a bar graph illustrating thatch layer thickness after seven months of laccase application on bentgrass in the field study. Laccase was applied every two weeks at different activity levels (units $cm^{-2}$). Laccase from Industrial source (CH I) and Jiangnan University (CH U) in China was also tested FIG. 13 is a bar graph illustrating thatch layer thickness after seven months of laccase application on bentgrass in the field study. Laccase was applied as 2.06 units $cm^{-2}$ at different frequency of application.

Figure 14:
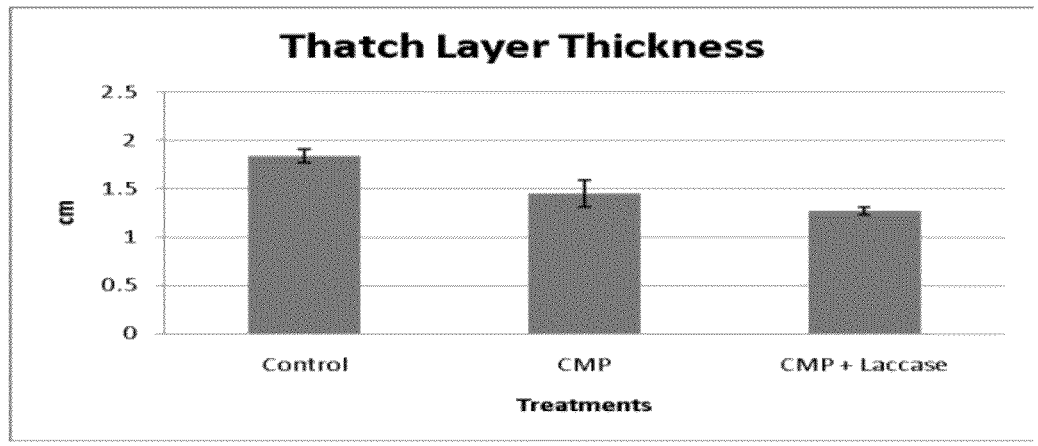

FIG. 14 is a bar graph illustrating thatch layer thickness after seven months of treatment application on bentgrass in the field study. Laccase was applied every four weeks at 2.06 units $cm^{-2}$. Cultural management practice (CMP) was core-aeration followed by sand topdressing. It was done once two months before the start of the experiment and once three months after the start of the experiment.

Figure 15:
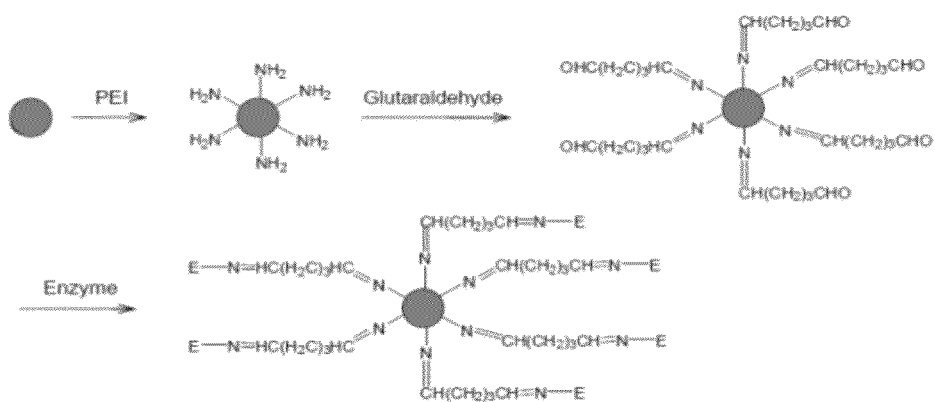

FIG. 15 is an illustration of a method of the present disclosure for immobilizing laccase enzyme on a particle of a particulate topdressing, such as sand, using glutaraldehyde as a linking agent.

FIG. 16 is illustrated in Table 1.
FIG. 17 is illustrated in Table 2.
FIG. 18 is illustrated in Table 3.
FIG. 19 is illustrated in Table 4.
FIG. 20 is illustrated in Table 5.

DESCRIPTION

The details of some embodiments of the present disclosure are set forth in the description below. Other features, objects, and advantages of the present disclosure will be apparent to one of skill in the art upon examination of the following description, drawings, examples and claims. It is intended that all such additional systems, methods, features, and advantages be included within this description, be within the scope of the present disclosure, and be protected by the accompanying claims Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, organic chemistry, biochemistry, genetics, botany, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

In describing and claiming the disclosed subject matter, the following terminology will be used in accordance with the definitions set forth below.

Having defined some of the terms herein, the various embodiments of the disclosure will be described.

As used herein the term "isolated laccase" or "isolated laccase enzyme" refers to a laccase enzyme that has been separated from its biological source (e.g., white rot fungi). The isolated laccase may or may not be combined in a formulation with other ingredients for application to turfgrass, thatch sample, or other lignin-containing sample. An isolated laccase may or may not be purified (e.g., free from other environmental contaminants, microbial secretes, or deactivated organisms), but it is separated from the source organisms or the source organisms have been deactivated.

As used herein, the term "thatch" refers to a layer of organic matter including tightly intermingled dead and living plant matter (e.g., stolons, rhizomes, roots, crown tissue, leaf sheaths and blades) located generally between the soil surface and the green vegetation (e.g., green turfgrass). As used herein, "thatch" may also include the mat layer (e.g., a layer of thatch intermixed with sand and/or soil).

The term "turf or "turfgrass", as used herein, refers to any vegetative ground covering, such as, but not limited to, various species of grasses used for lawns, fields, golf course grounds, and the like.

As used herein, "degrade" or "degrading" with respect to thatch, mat, or other lignin-containing sample indicates that the laccase enzymes are able to break-down portions of the chemical structure of the lignin-containing components of the sample or otherwise act to reduce the amount (measured by weight, thickness, or other measureable variable) of thatch, mat, and/or lignin content of the sample as compared to a sample not treated with the enzyme or the same sample prior to treatment with the laccase enzyme. Furthermore, "prevention" of thatch buildup, as used herein, indicates that application of a laccase enzyme, composition, or formulation of the present disclosure to a turfgrass reduces or eliminates the amount of thatch buildup over a predetermined period of time as compared to a similar turfgrass that is not treated with the laccase enzyme, composition, or formulation of the present disclosure.

As used herein, the terms "application" and/or "treatment" with respect to laccase enzyme compositions of the present disclosure refers to the act of contacting a specimen/sample (e.g., thatch sample, turfgrass sample, lawn, field, etc.) with a laccase enzyme composition of the present disclosure.

As used herein, the term "mediator" refers to compounds that help electron transfer during enzyme catalysis and thus enhance the efficiency of the enzyme. Exemplary mediators of laccase activity include, but are not limited to, guaiacol, catechol, ABTS, violuric acid, and the like.

The term "topdressing" as used herein, refers to a material applied to the top of a turfgrass ground covering, usually in an effort to obtain a desirable effect such as improved growth, color, health, or other turfgrass quality. Some examples of topdressing include sand or other particulate material often applied to turfgrasses for various purposes, including, but not limited to, management of soil moisture content.

Description:

Embodiments of the present disclosure include methods and compositions including isolated laccase enzymes to degrade and/or reduce turf thatch and/or to prevent the accumulation of turf thatch buildup.

Formation of thatch and mat layers represents a significant problem in turf management, such as golf course greens, sports fields, and lawns. Thatch is a layer of organic matter containing both living and dead plant tissues intermingled tightly with each other that accumulates between the soil and green turfgrass. It includes stolons, rhizomes, roots, crown tissue, leaf sheaths and blades (Engel, 1954). The mat layer is generally below the thatch layer where sand or soil is intermingled with thatch due to cultural practices like core aeration and top dressing (McCarty, 2005). Thatch management on greens is a critical aspect to long-term success of golf courses. Current methods are labor intensive, costly, and disruptive to play.

An appropriate amount of organic matter reduces turf surface hardness, moderates soil temperature extremes, increases the resilience and improves wear tolerance of turfgrass surface (Beard 1973), but excessive organic matter accumulation in the form of thatch-mat causes serious problems and represents a challenging turf management issue. High organic matter content reduces movement of oxygen through the thatch or mat zone, decreases saturated hydraulic conductivity, and increases water retention (Carrow, 2003). These primary problems further lead to some secondary problems like wet wilt, soft surface, black layer, limited rooting, and extra- and intra-cellular freezing damage (Carrow, 2004; O'Brien and Hartwiger, 2003). A cause of problems in the thatch-mat layer of golf greens, particularly in hot, humid summer periods, is the rapid change in the nature of organic matter from the structured organic matter in live plant tissues to the unstructured organic matter in dead plant tissues. Although live organic matter is supposed to have no adverse effect on the soil physical properties, the dead gelatinous organic matter swells in the presence of water during decomposition and plugs the soil macropores (air-filled pores). This causes a rapid decrease in the infiltration rate and oxygen levels in the root zones (Carrow, 2004; O'Brien and Hartwiger, 2003). The low oxygen levels (anaerobic conditions) further reduce the organic matter decomposition. Grasses generally produce more adventitious roots (surface roots) during anaerobic conditions that further increase organic matter content in the surface soil layer and exacerbate the situation.

Cultural or mechanical practices like core-aeration, vertical mowing, grooming, and top dressing have been used to attempt to manage thatch-mat buildup but are not sufficiently effective. Past studies have shown contrasting results in terms of thatch-mat reduction by various cultural practices (Carrow et al., 1987; Dunn et al., 1981; McCarty et al., 2005). On the other hand, these cultural practices are intensive in terms of cost, energy, and labor and can result in adverse effects on turfgrass quality and interfere with use of the turfgrass site (Landreth et al., 2008; McCarty et al., 2007). Several non-destructive thatch control studies using glucose, cellulase solutions (Ledeboer and Skogley, 1967) and commercial inocula containing various microorganisms (Murdoch and Barr, 1976; McCarty et al., 2005) were ineffective in reducing the amount of thatch.

Thatch-mat layers can result from a more rapid rate of organic matter accumulation than degradation (Beard, 1973). As such, studies have been carried out to enhance biodegradation of organic matter. This is usually done by inoculating microbial strains and supplementing nutrients. Past studies, however, have indicated that the results of biodethatching are highly variable from case to case (Ledeboer and Skogley, 1967; McCarty et al., 2005). These approaches have very limited utility in decreasing thatch because microorganisms are highly dependent on environmental conditions, making it difficult to maintain a stable population of specific organisms on a golf course green. For instance, microbial degraders, as living organisms, are highly dependent on natural conditions such as pH, moisture, aeration, redox, nutrients, competing organisms, and pesticide use. Additionally, many of the microbes used are only capable of degrading cellulose and hemicelluloses. The presence of lignin in plant cell walls limits the accessibility of microorganisms to the more biodegradable plant materials (cellulose and hemicelluloses). Lignin is a 3-dimensional amorphous polymer including a random and unorganized structure that serves as a barrier in plant cell walls to limit the accessibility to the more biodegradable plant materials, such as cellulose and hemicelluloses, by microbial degraders (Ledeboer and Skogley, 1967).

Natural degradation of lignin is carried out in the environment by organisms such as, but not limited to, white-rot fungi, which excrete extracellular lignolytic enzymes that solubilize and mineralize lignin (Kirk et al., 1975). Such enzymes preferentially attack lignin rather than cellulose or hemicellulose in the wood tissue (Mester et al., 2004; Blanchette, 1984). This process of selective delignification exposes cellulosic materials for further bacterial degradation in the environment (Otjen and Blanchette, 1987). Thatch is high in lignin, and for this reason, turfgrass species high in lignin content are resistant to decomposition (Ledeboer and Skogley, 1967; Beard, 1973).

The present disclosure describes the use of isolated lignin-degrading enzymes, such as fungal laccases, that directly attack lignin, thereby helping to effectively reduce the thatch layer buildup in turf greens. This enzymatic dethatching is more effective and reliable than previous cultural or mechanical practices and the use of living microbes (e.g., bacteria or live fungi) for various reasons. For one, enzymes, unlike living organisms, are relatively less sensitive to environmental conditions, and the use of pesticides, while damaging to specific living organisms, does not affect the isolated enzymes. Furthermore, the enzymes cause much less, if any, physical damage to turf than many mechanical methods such as vertical mowing and core-aeration. Additionally, even if mechanical and cultural practices, such as core-aeration, vertical mowing, or application of topdressing are used, the combination of such practices with the application of the enzyme compositions of the present disclosure will produce improved results over the use of the other practices alone. Laccase-facilitated dethatching can provide an effective and non-disruptive strategy for managing thatch on turfgrass, such as on lawns, sports fields, and golf greens.

In an embodiment of a method of degrading, reducing, and/or preventing turf thatch according to the present disclosure, a composition comprising an isolated fungal laccase enzyme is applied to turf thatch. The application of the laccase enzyme helps to degrade lignin in turf thatch and thereby reduce and/or prevent the buildup of excessive thatch that causes many problems for various turfgrasses. In an embodiment, the isolated fungal laccase enzyme is from white rot fungi. In an embodiment, the isolated fungal laccase enzyme is from the white rot species *Trametes versicolor* (e.g., laccase available from Sigma-Aldrich). In another embodiment the isolated laccase enzyme is a laccase enzyme obtained from Wuxi AccoBio Biotech, Inc. (Wuxi, China). In other embodiments, the isolated laccase enzyme is the partially purified isolated laccase enzyme produced by fungal fermentation and membrane purification (provided by Dr. Xiangru Liao, of Jiangnan University, China), which is isolated from an unknown fungal species that may be from the *Pycnoporus* genus. Other possible sources of laccase enzyme include, but are not limited to, other natural sources of laccase enzyme as well as another cell or organism, such as, for example, *e. coli*, that is adapted to produce laccase, e.g., genetically engineered by transformation with a construct containing a gene for laccase.

In embodiments of the present disclosure, the enzyme compositions may contain a mediator. Such mediators may improve the efficiency of the enzyme. Mediators are compounds used by the enzyme in reactions to break down lignin and/or other thatch materials. Any mediators of fungal laccase may be included to aid reactions catalyzed by the laccase leading to degradation of turf thatch. Some mediators may include, but are not limited to, catechol, guaiacol, ABTS, violuric acid, and 1-Hydroxy-benzotriazole (HBT).

In embodiments of the present disclosure the isolated laccase enzyme is added to irrigation water such that the amount of enzyme applied to the turf thatch is about 0.206, or 2.06 units/cm² of turf area. In embodiments, the amount of enzyme applied is at least about 0.206 units/cm² of turf area. In embodiments the amount of enzyme applied is from about 0.1 to about 20 units/cm², though this is not an upper limit, and higher rates could be used in some applications since no phytotoxicity has been observed. The enzyme may be applied in various formulations, including, but not limited to, a dry powder, a solution (e.g., a crude fermentation solution containing the enzymes), a solution of isolated enzyme diluted with water, or a composition where the enzyme is immobilized to a particulate material, as discussed below, and the like.

In embodiments of a method of the present disclosure for degrading turf thatch, the composition including isolated fungal laccase is applied to turf thatch at intervals as often as about once a week or as little as once a year. In some embodiments, applications could be as frequent as daily and as infrequent as a single application. In embodiments, applications may be performed in intervals as seldom as one application about every 56 weeks to as often as an application about once a week. In some embodiments, the isolated fungal laccase enzyme is applied about every 2 weeks to every 12 weeks. In practice, the timing of applications may be adjusted as determined by one of skill in the art.

The present disclosure also includes compositions for reducing turf thatch. In embodiments, the compositions include isolated laccase enzymes. In embodiments, the isolated fungal laccase enzyme is from white rot fungi. The laccase enzyme may be obtained from sources such as, but not limited to, those discussed above.

In embodiments, compositions of the present disclosure include isolated laccase enzyme that can be applied to turfgrass. In some embodiments, isolated laccase enzyme is included in a formulation already adapted for direct application to turfgrass (such as a lawn). In such embodiments, the formulation may include water, and/or other carriers, stabilizers, diluents and/or other ingredients, such as, but not limited to, those that enhance degradation of organic matter or those that serve other purposes for enhancing turfgrass quality (e.g., fertilizers, weed killers, and the like). Other embodiments include a formulation including isolated laccase enzyme that is formulated so that it can be diluted with water or other ingredients before or during application. In embodiments, the composition may be a liquid formulation with the laccase enzyme diluted with water or other liquid carrier for application via a sprayer or other liquid application device. In embodiments a formulation of the present disclosure includes a concentration of about 0.001% to 1% isolated laccase enzyme.

In embodiments, the laccase enzyme or formulation could be included as a component in combination with other lawn care products (example weed and feed products contain herbicide impregnated fertilizer. In other embodiments, the laccase enzyme may be provided in a dry powder formulation or in formulations in which the laccase enzymes are encapsulated, immobilized to carriers, or modified with stabilizers and dispersants for application to the lawn. In yet other embodiments, compositions of the present disclosure include a particulate topdressing, where the laccase enzyme is immobilized to particles of the particulate topdressing. The particulate topdressing may include various topdressings used for application to turfgrass, such as, for instance, sand, synthetic granules, diatomaceous earth, calcined clay, ground corn cobs or other organic materials, silica/quartz sand, zeolite, lassinite, resins, and the like.

In an embodiment, the particulate topdressing is sand and the isolated fungal laccases are immobilized to sand particles.

In embodiments, laccase enzymes are immobilized to particles of topdressing (e.g., sand, or other natural or synthetic particulate material) by activating the sand or other particulate topdressing with a linking material, such as but not limited to, chitosan and/or gluteraldehyde to activate the particle surface for enzyme attachment. Next, the enzymes are immobilized to the particles via the chitosan and/or glutaraldehyde. In an example embodiment (described in greater detail in Example 5, below), the surfaces of the particles are first activated with polyethyleneimine followed by crosslinkage with gultaraldehyde to graft aldehyde groups onto the surface of the particle. Then enzymes can be covalently bonded to the particles by reaction between the aldehyde groups and free amino groups on protein surface.

In other embodiments, a layer-by-layer (LbL) assembly approach can be used to immobilize the enzymes on the particle surface. This embodiment involves alternate sorption of a polycation substrate, a polyanion substrate, and the enzyme onto the particles. For application of each layer pH is controlled to provide the substrates and/or the enzyme with the appropriate charges. Each sorption step leads to a reversal of the terminal surface charge after adsorption of a new layer. In embodiments the particles are coated with alternating layers of a polycation, a polyanion, and the enzyme, such that the enzyme is captured between layers on the particle. One example of a conventional LbL method is described in Example 5 below where poly(allylamine hydrochloride) (PAH) and poly(sodium 4-styrenesulfonate) (PSS) are used as the polyanions and polycations, respectively. The pH of the enzyme solution is carefully adjusted to several units away from their respective isoelectric points to maintain a net negative or positive charge. Sequential polyelectrolyte/enzyme layers are deposited to form repetitive particle-PAH-PSS-enzyme or particle-PAH-PSS-PAH-enzyme sandwich. For each assembly step, the polyelectrolyte/enzyme is allowed to equilibrate with the sand particles before the next layer is added.

In other embodiments, laccase enzymes can be immobilized to the particles of topdressing by methods known to those in the art for immobilizing proteins to solid surfaces. In embodiments where isolated laccase enzymes are immobilized to a topdressing formulation, frequency of application may be reduced (e.g., to as little as about once every 12 months or even less, depending on the location, application, etc.).

Now having described the embodiments of the present disclosure, in general, the Examples, below, describe some additional embodiments of the present disclosure. While embodiments of the present disclosure are described in connection with the Examples and the corresponding text and figures, there is no intent to limit embodiments of the present disclosure to these descriptions. On the contrary, the intent is to cover all alternatives, modifications, and equivalents included within the spirit and scope of embodiments of the present disclosure.

EXAMPLES

Example 1

Laboratory Study

Thatch was collected from bentgrass pots in a greenhouse at Griffin, Ga. Thatch was cut into five by five cm squares and air dried. Dried thatch was ground with a coffee grinder and was passed through a 20-mesh sieve at the top and 80-mesh sieve at the bottom. The sieves were shaken for 15 minutes.

The material left on the top of 20-mesh was reprocessed and material below 80-mesh was discarded. The material retained on 80-mesh was retained and used for analysis.

A 300 mg portion of thatch was weighed in each of 18 Petri plates. Ten ml of six different concentrations of laccase 0 (control), 2, 4, 6, 8 and 10 units/ml was added to Petri plates everyday as triplicates for seven days. One unit activity of laccase equals the amount of enzyme that causes the absorbance change in 468 nm at a rate of 1.0 unit/min in 3.4 ml of 1 mM 2,6-dimethoxyphenol in citrate-phosphate buffer at pH3.8 (Park et al., 1999). For this and the other examples, the laccase enzyme is produced by Sigma-Aldrich (Sigma Aldrich Inc., St. Louis, Mo.) and is from the white rot fungi *Trametes versicolor*.

Extractive-free ASL and AIL content in the thatch sample was determined in a two-step hydrolysis procedure according to the laboratory analytical procedure developed by The National Renewable Energy Laboratory (NREL, 2008). In the first step, extractive free thatch samples were hydrolyzed for 60 min with 72% $H_2SO_4$ at 30° C. In the second step, $H_2SO_4$ was diluted to 4% and the samples were autoclaved at 121° C. for 1 h. Acid-soluble lignin was determined using this hydrolysis liquid at 240 nm wavelength in a UV/VIS spectrophotometer. The solids remaining after acid hydrolysis were dried in an oven at 100±5° C. for 24 h, weighed, ashed in a muffle furnace at 600±25° C. for 24 h, and weighed again. Weight difference was used to calculate the acid-insoluble lignin content.

Figure 1:
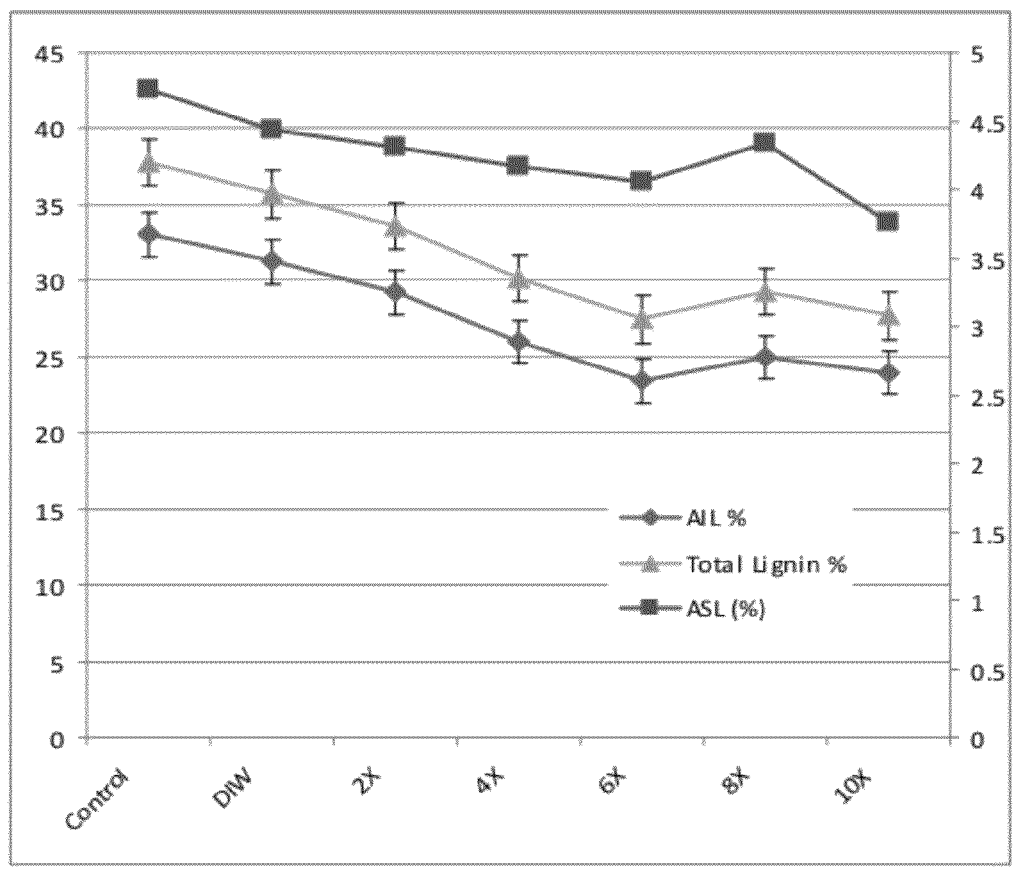
FIG. 1 is a graph illustrating lignin contents of thatch materials that have received laccase treatment at different concentrations (0, 2, 4, 6, 8, 10 units $mL^{-1}$) for seven days.

Results:

There was a significant decrease in the acid-soluble lignin content with increasing levels of laccase activity. There was a 20.5 percent decrease in acid soluble lignin in thatch sample treated with 10 units/ml of enzyme as compared with the control. Acid-insoluble lignin and total lignin content decreased significantly with increasing levels of enzyme activity up to 6 units/ml activity of laccase. Acid-insoluble lignin and total lignin content decreased by 18.5 and 26.6 percent, respectively as compared to control. The results, shown in FIG. 1, clearly indicate that the lignin content was reduced as a result of laccase treatment, and the reduction appeared to increase as the enzyme level increased.

Example 2

Greenhouse Study

Formation of high organic content in the form of thatch and/or mat layer is a major problem in management of turfgrass golf greens. A greenhouse experiment was conducted on potted bentgrass to determine the efficacy of a ligninolytic enzyme, laccase, in effectively reducing organic matter in thatch-mat layer. Laccase was added biweekly at activity levels of 0, 0.206, 2.06 and 20.6 units $cm^{-2}$ area with and without guaiacol, a mediator of laccase believed to enhance enzyme performance, and sampling was performed after two and nine months of treatment. The parameters investigated include thickness of organic layer, thatch layer, mat layer, total organic carbon at different depths, saturated hydraulic conductivity, and lignin content. After two months, a significant reduction of 8.7 and 8.4% for organic layer thickness and extractive-free total lignin content, respectively, were observed with laccase activity level of 20.6 units $cm^{-2}$ area in comparison to control. After nine months, we observed a 15.6, and 45.0% decrease in organic and thatch layer thickness, respectively, at laccase activity level of 2.06 units $cm^{-2}$ area. At the same laccase activity level with guaiacol application, a reduction of 32.1 and 6.4% and an increase of 322% were observed for total organic carbon (0-2.5 cm depth), total lignin content, and saturated hydraulic conductivity, respectively. The 0.206 units $cm^{-2}$ area activity level of laccase did not appear to demonstrate significant effect after nine months of application. Applications did not negatively affect turf quality. The positive response of laccase at the activity level of 2.06 units $cm^{-2}$ area suggest that this could be a non-disruptive option for thatch and/or mat control in bentgrass.

Introduction

Thatch is a layer of organic matter containing both living and dead plant tissues intermingled tightly with each other that accumulates between the soil and green turfgrass. It includes stolons, rhizomes, roots, crown tissue, leaf sheaths, and blades (Engel, 1954; Roberts and Bredakis, 1960). The mat layer is generally below the thatch layer and differs due to presence of sand or soil intermingled with thatch as a result of cultural practices like core aeration and top dressing (McCarty, 2005). A small amount of organic matter reduces surface hardness, moderates soil temperature extremes, increases the resilience, and improves wear tolerance of turfgrass surface (Beard 1973); however, excessive thatch and mat layers are undesirable in turfgrass.

High organic matter accumulation in the form of thatch-mat causes problems like decreased movement of oxygen through the thatch or mat zone, decreased saturated hydraulic conductivity, and increased water retention (Carrow, 2003; Hartwiger, 2004; McCarty et al., 2007). These primary problems may further lead to some secondary problems like wet wilt, soft surface, black layer, limited rooting and extra- and intra-cellular freezing damage (Beard, 1973; Carrow, 2004; O'Brien and Hartwiger, 2003). Although structured organic matter, present in live underground plant tissues, is supposed to have no adverse effect on the soil physical properties, rapid root death that results in dead gelatinous organic matter swells in the presence of water during decomposition and plugs the soil macro-pores (air-filled pores), causing low oxygen levels in the root zones (Carrow, 2004; O'Brien and Hartwiger, 2003). Increased accumulation of organic matter causes anaerobic conditions, which further reduce the rate of organic matter decomposition (McCoy, 1992). Grasses generally produce more adventitious roots (surface roots) during anaerobic conditions, further increasing organic matter content.

Cultural or mechanical practices like core-aeration, vertical mowing, grooming, and top dressing have been used to manage the thatch-mat buildup but are not sufficiently effective in most cases in reducing organic matter accumulation (Carley et al., 2011). Past studies have shown contrasting results in terms of thatch-mat reduction by various cultural practices (Barton et al., 2009; Carrow et al., 1987; Dunn et al., 1981; McCarty et al., 2005; McWhirter and Ward, 1976; Weston and Dunn, 1985; White and Dickens, 1984). These cultural practices are intensive in terms of cost, energy, and labor as well as have adverse effects on turfgrass quality (Barton et al., 2009; Landreth et al., 2008; McCarty et al., 2007). Several non-destructive thatch control studies using glucose, cellulase solutions (Ledeboer and Skogley, 1967) and commercial inocula containing various microorganisms were ineffective in reducing the amount of thatch (Murdoch and Barr, 1976; McCarty et al., 2005). However, reduction in cellulose content and total oxidizable organic matter of bermudagrass and centipedegrass (Sartain and Volk, 1984) and weight loss of bermudagrass pellets, St. Augustine grass and zoysiagrass stolons (Martin and Dale, 1980) were observed when inoculated with different wood-decaying fungi under controlled greenhouse and laboratory conditions. However, field inoculation experiments on bermudagrass showed no thatch degradation (Martin and Dale, 1980).

The formation of the thatch-mat layer is due to a greater rate of organic matter accumulation than degradation (Beard, 1973). Most microbial degradation mechanisms are restricted by the presence of lignin, a plant cell wall constituent. The slow decomposition of soil lignin has long been recognized (Kirk and Farrel, 1987). Lignin is a three-dimensional amorphous polymer including a random and unorganized structure that serves as a barrier in the cell walls limiting accessibility of microbial degraders to the more biodegradable plant materials, such as cellulose and hemicelluloses (Ledeboer and Skogley, 1967). Lignin is formed in plants by oxidative coupling of mono lignols of three primary hydroxycinnamyl alcohols: p-coumaryl, coniferyl and sinapyl alcohols. The corresponding lignin monomers are known as p-hydroxy phenyl, guaiacyl and syringyl units, respectively (Wong, 2009). Lignification is achieved by cross linking of monomers with a growing polymer via polymer-polymer coupling. Based on the random coupling theory, several models of lignin molecular structure have been proposed but these models do not imply any particular sequence of monomeric units in the lignin macromolecule (Davin and Lewis, 2003; Chen and Sarkanen, 2003).

Natural degradation of lignin is carried out in the environment by some organisms, such as white-rot fungi, which solubilize and mineralize lignin with the help of lignolytic enzymes (Kirk et al., 1975; Kirk et al., 1976). White-rot fungi preferentially attack lignin more than cellulose or hemicellulose in the wood tissue (Mester et al., 2004; Blanchette, 1984). This process of selective delignification exposes cellulosic materials for further bacterial degradation in the environment (Otjen and Blanchette, 1987). Due to higher lignin content in thatch layer in comparison to the live grass tissues, thatch layer in turfgrass species high in lignin content is more resistant to microbial decomposition (Ledeboer and Skogley, 1967; Beard, 1973). The present example demonstrates that the use of isolated lignin-degrading enzymes, such as fungal laccases, can effectively reduce the thatch layer buildup in turf greens. The study confirms two hypotheses: 1) degradation of soil organic matter can be enhanced by laccase application; and 2) application of laccase enzyme has no adverse effect on turf quality.

Materials and Methods

A greenhouse experiment was conducted using "Crenshaw" creeping bentgrass, *Agrostis stolonifera*, established in pots (top diameter 15 cm, height 11.5 cm) at the University of Georgia, Griffin campus from October 2008 to July 2009. The bentgrass was acquired from East Lake Country Club, Atlanta, Ga. and was grown on 85:15 sand and organic matter mix. All the pots were irrigated daily, fertilized monthly as a 50 mL solution of 0.4% (w/v) macron water soluble 28-7-14 fertilizer (Lesco. Strongsville, Ohio), and maintained at a height of 2.5 cm. The refrigerated air conditioned greenhouse was maintained at 25±2/18±2° C., day/night temperature. For the first two months, the treatments were five replications of eight factorial combinations of four levels of laccase and two levels of guaiacol. Four laccase activity levels were 0 (control), 0.206, 2.06, and 20.6 units $cm^{-2}$ area. The treatments after the two month sampling were six factorial combinations of four replications of three levels of laccase and two levels of guaiacol. Three levels of laccase activity were 0, 0.206 and 2.06 units $cm^{-2}$ area. Each treatment was further divided into two groups, one group that received 10-mL of 0.1 M guaiacol along with enzyme treatments and one group that did not. Guaiacol is a natural co-substrate as well as mediator of laccase which is believed to enhance enzyme performance (Roper et al., 2000). Laccase was sprayed as a 40-mL solution of different activity levels, and control was sprayed by 40-mL distilled water on bentgrass.

Laccase Activity Assay

Laccase enzyme from *Trametes versicolor*, a white-rot fungus, was purchased from Sigma-Aldrich (Sigma Aldrich Inc., St. Louis, Mo.). The activity of laccase was quantified using a UV/VIS-spectrophotometer by a colorimetric assay. One activity unit of laccase corresponds to the amount of enzyme that causes the absorbance change in 468 nm at a rate of 1.0 unit $min^{-1}$ in 3.4 mL of 1 mM 2,6-dimethoxyphenol in citrate-phosphate buffer at pH 3.8 (Park et al., 1999). Laccase activity levels of 0 (control), 0.206, 2.06 and 20.6 units $cm^{-2}$ area actually corresponds to activity levels of 0, 0.912, 9.12 and 91.2 units $mL^{-1}$ laccase solutions, respectively. The activity level of laccase per unit area is calculated by dividing total number of units in the laccase solution by the surface area of the pot.

Measurements

The variables measured after two and nine months of treatment are listed, respectively, followed by brief description of the methods for the measurements.

Measured Variables Common to Both Sampling Durations

Effectiveness of treatments was determined by measuring organic layer thickness (OLT), total organic carbon content (TOC) for a depth of 0-5.0 cm, extractive-free acid-soluble (ASL) and -insoluble lignin (AIL) content after two and nine months of treatment application. Total lignin (TL) was obtained by addition of acid-soluble and -insoluble lignin content.

Additional Variables Measured after Nine Months of Treatment Application

After nine months of treatment application, OLT was subdivided into thatch layer thickness (TLT) and mat layer thickness (MLT), TOC was subdivided for 0-2.5, and 2.5-5.0 cm depth to better reflect the effectiveness of laccase on thatch-mat layer reduction. Saturated hydraulic conductivity (SHC) was also measured.

Turf Quality

Turf quality was determined bi-weekly for first three months and the last two months to observe any phytotoxicity due to laccase application.

Organic Layer Thickness and Thatch-Mat Layer Thickness

The thickness (OLT, TLT, and MLT) was measured from seven different locations around the edges on each pot and then averaged. The thatch layer was observed above the mat layer.

Total Organic Carbon Content

The measurement of TOC was done as described by Carrow et al. (1987). Soil cores were dried in an oven at 100±5° C. for 48 h and weighed. Soil cores were ashed in a muffle furnace at 600±25° C. for 24 h and weighed again. Total organic carbon content was determined as the difference in the two readings and percent total organic carbon was calculated for statistical analysis.

Saturated Hydraulic Conductivity

Intact cores were obtained from the center of each pot using a soil corer. The cores were obtained in brass rings. The bottom of the core was covered with a double layer of cheesecloth held in place with a rubber band. The core was saturated overnight in a 0.05 N $CaCl_2$ solution. A clear plastic cylinder of the same diameter as of the brass ring was fastened above the brass ring with paraffin wax tape. The SHC of the cores was measured by a constant hydraulic head method using a Marriott tube apparatus. A time of 10-minutes was allowed for the establishment of steady state flow through the samples. Volume of water that passed through the core was measured for one minute and repeated three times. Saturated hydraulic conductivity was calculated using Darcy's equation.

Extractive-free Lignin Content

Thatch was collected from each pot from the top 2.5 cm after sampling for TOC and SHC. Extractive-free ASL and AIL content in the thatch layer was determined in a two-step hydrolysis procedure according to the laboratory analytical procedure developed by The National Renewable Energy Laboratory (NREL, 2008). In the first step, extractive free thatch samples were hydrolyzed for 60 min with 72% $H_2SO_4$ at 30° C. In the second step, $H_2SO_4$ was diluted to 4% and the samples were autoclaved at 121° C. for 1 h. Acid-soluble lignin was determined using this hydrolysis liquid at 240 nm wavelength in a UV/VIS spectrophotometer. The solids remaining after acid hydrolysis were dried in an oven at 100±5° C. for 24 h, weighed, ashed in a muffle furnace at 600±25° C. for 24 h, and weighed again. Weight difference was used to calculate the acid-insoluble lignin content.

Turf Quality

The potential for phytotoxicity of each treatment was recorded every two weeks by rating turf quality and canopy spectral reflectance. Visual turf quality ratings were rated on the basis of color, shoot density, and uniformity. Turf quality was rated on a numerical score where 1 equals no live turf and 9 equals ideal dark green, uniform turf (Johnson et al., 1987). Grass index was determined using TCM 500 turf color meter (Spectrum Technologies, Plainfield, Ill.). Grass index is a numerical score of the color and density of grass based on the spectral reflectance at 660 and 850 nm. Three grass index readings were recorded from each pot and averaged for statistical analysis.

Statistical Analysis

A completely randomized factorial design was used to analyze the full model, a three factor study consisting of two levels of treatment duration, three levels of laccase, and two levels of guaiacol. Similarly, a two factor study consisting of four levels of laccase enzyme and two levels of guaiacol for the first two months and three levels of laccase enzyme and two levels of guaiacol for nine months of treatment application was analyzed. Analysis of variance (ANOVA) was performed to evaluate the main effects of treatment duration, laccase, and guaiacol and interaction effects of these three factors using general linear model (GLM) (SAS Institute, 1989). Fisher's LSD test with $\alpha=0.05$ was used for obtaining means separation Results The results will be explained on the basis of the Anova table (Table 1 (FIG. 16)). The result section will be divided into full model, two, and nine months of treatment application.

Full Model

The full model was used to compare the parameters at two sampling dates. The model includes the main and interaction effects of treatment duration, three levels of laccase, and two levels of guaiacol for OLT, TOC (0-5.0 cm), ASL, and AIL. Three levels of laccase were used, as laccase treatment at activity level of 20.6 units $cm^{-2}$ was discontinued after two months of application.

A significant effect of treatment duration, and interaction of treatment duration and laccase treatments was observed on OLT, TOC (0-0.5 cm), and ASL (Table 1 (FIG. 16)). However no significant effect was observed for AIL. Laccase application was found to have significant effect on OLT, TOC (0-5.0 cm), ASL and AIL at 0.1% level of significance. However, guaiacol treatment as well as interaction of guaiacol and treatment duration did not appear to have significant effect on the tested parameters. An increase of 43.2, 23.6, and 20.9% in OLT was recorded in control pots and pots treated with 2.06 units $cm^{-2}$ area laccase, without and with guaiacol, respectively, in between the two sampling dates of two and nine months after initiation (FIG. 2 and Table 2 (FIG. 17)). Overall, there was an increase of 46.9 and 23.7% in TOC (0-5.0 cm) exhibited between two sampling dates for control and laccase activity level of 2.06 units $cm^{-2}$ area, respectively (FIG. 2 and Table 2 (FIG. 17)).

Two Months

After two months of treatment application, the effect of laccase was significant at 0.1% level of significance for ASL and AIL (Table1). There was no effect of laccase observed on OLT and TOC (0-5.0 cm). However, there was a 15.6% reduction in OLT with laccase activity level of 20.6 units $cm^{-2}$ area without guaiacol, in comparison to control (Table 2 (FIG. 17)). Other treatments showed no effect on OLT. Guaiacol and interaction effect of laccase and guaiacol had no significant effect on any of the parameters (Table 1 (FIG. 16)). A reduction of 11.9, 7.8, and 8.4% for ASL, AIL and TL content, respectively, after two months of application was observed for laccase activity of 20.6 units $cm^{-2}$ area without mediator (Table 3 (FIG. 18)). Similarly, a reduction of 9.6, 7.3, and 7.7% for ASL, AIL, and TL was found at same laccase activity level along with guaiacol. Laccase activity level of 2.06 units$^{-2}$ area with guaiacol also showed significant reduction for ASL.

Nine Months

After nine months of treatment application, a significant effect of laccase application was observed for OLT, TLT, TOC (0-5.0, and 0-2.5 cm), ASL, AIL and SHC at 0.1% level of significance (Table 1(FIG. 16)). A significant effect of guaiacol was observed for ASL and SHC at 5 and 1% level of significance, respectively (Table 1 (FIG. 16)). Interaction effect of laccase and guaiacol was observed for SHC at 0.1% level of significance. However, no effect was observed for MLT and TOC (2.5-5.0 cm) after nine months of treatment application.

A decrease of 14.5 and 13.0% was observed in OLT with laccase activity level of 2.06 units $cm^{-2}$ area with and without guaiacol, respectively, in comparison to control (Table 2 (FIG. 17)). Similarly, a 45 and 35% decrease in TLT was observed with laccase activity level of 2.06 units $cm^{-2}$ area with and without guaiacol, respectively, as compared to control. The treatment with 2.06 units $cm^{-2}$ area of laccase activity was significantly different in comparison to control as well as to 0.206 units $cm^{-2}$ area of laccase activity (FIG. 3).

A reduction of 15.4 and 15.8% (TOC 0-5.0 cm), 27.4 and 32.1% (TOC 0-2.5 cm) was observed at the laccase activity level of 2.06 units $cm^{-2}$ area with and without guaiacol, respectively, as compared to control (FIG. 4 and Table 2 (FIG. 17)). Similarly, an increase of 322 and 94% over the control was recorded for SHC with treatment of laccase at activity level of 2.06 units $cm^{-2}$ area with and without guaiacol, respectively (FIG. 5). A reduction of 12.2, 5.4, and 6.4% for ASL, AIL and TL content, respectively, was observed for laccase activity of 2.06 units $cm^{-2}$ area without mediator (Table 3 (FIG. 18)).

Turf Quality

No significant differences in visual quality ratings were observed for all the treatments except for the data collected after thirty eight weeks where the treatment 2.06 units $cm^{-2}$ exhibited a significant but slight reduction in turf quality in comparison to the control treatment (Table 4 (FIG. 19)). No significant differences in any treatment in comparison to control was observed when the data was analyzed as the average of data collected before (early) and after (late) the first sampling as well as the average of the whole (all) data (Table 4

(FIG. 19)). For grass index values, a decrease was observed initially after four and six weeks of treatment application at laccase activity level of 20.6 units cm$^{-2}$ area in comparison to control. However, no significant differences in grass index values were observed after six weeks of treatment application (Table 5 (FIG. 20)).

Discussion

To the best of our knowledge, this is the first study using laccase enzyme to manage thatch-mat accumulation on turf grass. Application of laccase, especially at the 2.06 units cm$^{-2}$ area activity level, proved to be effective in reducing thatch-mat depth, TOC, and significantly increasing SHC. Carley et al. (2011) noted that the nature of temporal dynamics of organic matter accumulation was for small annual changes resulting in long term effects. Our results indicate that laccase application could result in altering organic dynamics in a positive manner with the 2.06 units cm$^{-2}$ area activity level of laccase effective in reducing TLT, and TOC (0-2.5 cm). This treatment also resulted in increasing SHC after nine months of application where a three and two fold increase in SHC was observed with laccase activity level of 2.06 cm$^{-2}$ area with and without guaiacol, respectively. This increase can be explained on the basis of thatch layer thickness of the corresponding treatment. Thatch layer depth more than 1.3 cm was reported to adversely affect water infiltration (McCarty et al, 2005). Thatch layer thickness for the treatment 2.06 units cm$^{-2}$ area with and without guaiacol after nine months of treatment was 1.1 and 1.3 cm, respectively. For both two and nine months sampling, no effect of guaiacol and interaction effect of laccase and guaiacol was observed except for saturated hydraulic conductivity after nine months of application.

The lowest level of laccase application (0.206 units cm$^{-2}$ area) did not appear to have significant effect at nine months after application for the parameters tested. Laccase activity level of 20.6 unit cm$^{-2}$ area was applied for two months and was effective in significant reduction of OLT and extractive-free lignin content (ASL, AIL, and TL) of the thatch layer.

Laccase application had only minor influence on turfgrass quality. An initial but slight reduction in turf quality was observed during the first four to six weeks for grass index values at the activity level of 20.6 units cm$^{-2}$ area. However, visual quality ratings were not significantly different except for one treatment at 33 weeks.

If laccase was effective in enhancing organic matter degradation, it would seem reasonable to expect that effects would become more apparent over time. Samples were analyzed after two and nine months of treatment application. Laccase activity levels of 0.206 and 2.06 units cm$^{-2}$ area were continued for nine months. It was observed that time duration, and interaction of time duration and laccase had significant effect on OLT, TOC (0-5.0 cm), and ASL content with laccase activity level of 2.06 units cm$^{-2}$ area. However, for the other laccase activity level, there was no apparent effect of time of application on any of the measurements.

Studies in the past using various cultural management practices with different cultivation frequencies have reported contrasting results for reduction in thatch-mat accumulation (Callahan et al., 1998; Carrow et al., 1987; Engel and Alderfer, 1967; McCarty et al., 2005; Rieke, 1994). Degradation of thatch-mat is reported either in terms of thatch-mat depth (Soper et al., 1988; Smiley et al., 1985) or in terms of thatch-mat depth and organic matter content by weight (Barton et al., 2009; McCarty et al., 2007). The organic matter content by weight in different studies is observed for different depths further making it difficult to compare the results (Barton et al., 2009; McCarty et al., 2005; Murray and Juska, 1997). In our study, however, we observed both organic layer thickness (thatch layer and mat layer) and total organic carbon content for better comparison of effectiveness of laccase on thatch-mat degradation.

Cultural practices like core-aeration and vertical mowing are disruptive in nature and have shown to reduce the turf quality both aesthetically and physically, further reducing the playability of the turf (Barton et al., 2009; Landreth et al., 2008; McCarty et al., 2007). However application of laccase is not disruptive and the effective treatment of 2.06 units cm$^{-2}$ laccase activity for nine months of application showed no quality reduction on bentgrass.

Several non-destructive studies in the past using different chemicals like sugars, mixture of sugars and microbial inocula, and some enzyme like cellulase, proved ineffective (Ledeboer and Skogley, 1967; Murdoch and Barr, 1976; McCarty et al., 2005; Martin and Dale, 1980). Most of these studies intended to increase microbial population to degrade organic matter. But it is difficult to maintain higher microbial populations over sustained period of time under field turfgrass management systems due to the inability to maintain proper micro environment conditions required by particular microbial population. Other reason may be that previous studies were focused on degradation of cellulose and hemicellulose by using cellulase enzyme and by increasing bacterial population. Whereas, our hypothesis is that lignin degradation will open the cell wall structure and make cellulose and hemicellulose more available for further microbial degradation. In the present example isolated laccase enzyme, which is stable over a wide pH and temperature (Baldrian, 2006; Munoz et al., 1997; Stoilova et al., 2010; Hurston, 1994), from the white-rot fungi *Trametes versicolor* was employed to act on lignin and to facilitate dethatching, thereby reducing the dependence on microbial growth and climate fluctuations.

Conclusions

The greenhouse research demonstrated that bi-weekly application of laccase enzyme at the 2.06 units cm$^{-2}$ area can be effective in reducing buildup of organic matter in highly maintained turf. Duration of laccase application appeared to have an effect on thatch-mat management as judged by results at 9 month sample period. These findings indicated a novel approach to reduce organic matter in thatch or mat and its associated problems on golf greens and represent a new non-disruptive method for thatch management.

Tables for Example 2 appear at the end of the description.

Example 3

Greenhouse Study (Dead Grass)

Another greenhouse study was started in December 2009 on dead Bentgrass pots to provide more knowledge about the effects of laccase on organic matter degradation. When live grass is used, final thatch status is the net result of organic matter additions by the plant minus the degradation of organic matter. The current study allowed only degradation to be observed. Laccase was sprayed every two weeks at activity levels of 0, 2.06, and 20.6 units cm$^{-2}$, respectively. The pots were irrigated with distilled water containing 0 units/ml served as controls. The pots receiving, 2.06 and 20.6 units cm$^{-2}$ were further divided into two groups, one of which received guaiacol along with laccase. Guaiacol is a mediator of laccase, which is believed to enhance enzyme performance. For all treatments, ten replicates were prepared. Five replicates were sampled during Feb. 2010, after two months of treatment, and the other five replicates were sampled after six months of treatment. The results are presented in FIGS. 6,

7, and 8, and again confirmed the finding on live grass from Example 2, above, that the enzyme treatment effectively reduces thatch.

Example 4

Field Study

Introduction:

Conditions of laccase application identified through the green-house study were examined in field trials. This study was divided in two stages. Stage 1 focused on treatment optimization on bentgrass, bermudagrass, and zoysiagrass research greens at the UGA Griffin Campus, and stage 2, data not yet available, will involve a series of trials on golf course greens.

The study illustrates process optimization targets at several process parameters that can potentially greatly reduce cost in management of turfgrass. Optimization of enzyme application rate dosages and frequency was examined to achieve desirable dethatching effect with minimum amount of enzymes. Second, enzymes from three different sources that are prepared in different purity and have large difference in price per unit activity were tested. Third, a new enzyme delivery approach was developed in which laccase was immobilized to sand particle surfaces (see Example 5) and this delivery method will be tested by application to turf via sand topdressing. This immobilized form of enzymes has potential to remain in top thatch layer longer with less activity loss, thus reducing enzyme consumption.

The present example verifies the effectiveness of enzymatic dethatching on turfgrass in the field and produced data to help optimize the process to improve cost-effectiveness. While the previously described Examples were carried out in greenhouses, all experiments in this example were conducted in the field.

Materials and Methods:

Experiments were performed on a 20+ year old creeping bentgrass research green at the UGA Griffin Campus. As might be expected, this research green has significant thatch problems. Four different levels of laccase activity and four different levels of frequency of application were used. The laccase activity level of 2.06 units cm$^{-3}$, which proved to be effective in the previous greenhouse experiment, was tested. Each treatment was tested in four replications on 1×2 ft plots, and the arrangement of plots was randomized.

The activity of laccase was quantified using A UV/VIS-spectrophotometer by a colorimetric assay at an absorbance of 468 nm (Park et al., 1999) as described earlier in the green house study. The enzyme was applied by spraying 410 mL solution of laccase enzyme to each plot of size 2 ft$^2$ at a frequency of 2, 4, 8, and 12 weeks and rate of laccase activity level at 0.515, 1.03, 2.06, and 4. 12 units cm$^{-2}$ area.

Effectiveness of treatments was assessed by measuring thatch layer thickness, mat layer thickness, total organic carbon content, saturated hydraulic conductivity ($K_{sat}$), and extractive-free lignin content after six months and one year. Turf quality measurements were performed once every month.

Two soil cores per plot were used to measure thatch and mat layer thickness as well as total organic carbon content. The total organic carbon content was determined for the soil core depth of 0-2.5 cm and 2.5-5.0 cm, respectively, to get a better understanding of the effectiveness of laccase on thatch-mat layer reduction. The measurement of total organic content was done as described by Carrow et al. (1987). Soil cores were dried in an oven at 100±5° C. for 48 h and weighed. Soil cores were ashed in a muffle furnace at 600±25° C. for 24 h and weighed again. Total organic carbon content was determined as the difference in the two readings, and percent total organic carbon was calculated for statistical analysis.

In order to measure saturated hydraulic conductivity, intact cores were obtained from each plot using a soil corer. The cores were obtained in brass rings, and saturated overnight in a 0.05 N CaCl$_2$ solution. Saturated hydraulic conductivity of the cores was measured by a constant hydraulic head method using a Marriott tube apparatus. A time of 10-minutes was allowed for the establishment of steady state flow through the samples. Volume of water that passed through the core was measured at every one minute and repeated three times. Saturated hydraulic conductivity was calculated using Darcy's law equation.

Thatch was collected from each plot from the top 2.5 cm for lignin content measurement. Extractive-free acid-soluble and -insoluble lignin content in the thatch layer was determined in a two step hydrolysis procedure according to the laboratory analytical procedure developed by The National Renewable Energy Laboratory (NREL/TP-510-42618). In the first step, extractive free thatch samples were hydrolyzed for 60 min with 72% H$_2$SO$_4$ at 30° C. In the second step, H$_2$SO$_4$ was diluted to 4% and the samples were autoclaved at 121° C. for 1 h. Acid-soluble lignin was determined using this hydrolysis liquid at 245 nm wavelength in a UV/VIS spectrophotometer. The solids remaining after acid hydrolysis were dried in an oven at 100±5° C. for 24 h and weighed and then ashed in a muffle furnace at 600±25° C. for 24 h and weighed again. Weight difference was used to calculate the acid-insoluble lignin content.

The quality of the grass in each treatment was routinely analyzed at least once per month throughout the study by color quality assessment of digital images using SigmaScan software.

Enzymes from three different sources were tested. The first is the purified enzyme from Sigma-Aldrich (used in Example 2, above). The second source is a crude laccase produced by Wuxi AccoBio Biotech, Inc (Wuxi, China). The third is a partially purified form produced by fungal fermentation and membrane purification, which will come from Dr. Xiangru Liao, a professor in Bio-engineering in Jiangnan University, China. While the three different enzyme forms have different activity per mass, their enzymatic performance and stability are comparable as examined in preliminary tests. However the costs of the later two enzyme forms are 10-20 times lower than the purified enzyme from Sigma-Aldrich on a unit activity basis, with the third enzyme form potentially offering the best cost-effectiveness.

The experiments were performed at one enzyme rate dosage (normalized by activity) and frequency with all three enzyme forms on three different grasses (creeping bentgrass, bermudagrass and zoysiagrass). The enzymes were applied in solution via irrigation in the same manner described above, and again four replications were tested for each treatment. Effectiveness of treatments and turf quality were evaluated as described above.

Results and Discussion:

Field experiments began in June 2010 to determine the effectiveness of laccase enzyme in facilitating organic matter degradation under field conditions, and to determine the range of enzyme activity and enzyme application frequency that is effective for dethatching. The experiments were conducted on bentgrass, bermudagrass and zoysiagrass. Each experiment plot unit was two square feet, and laccase was applied as 410-mL solution, at different levels expressed as units per square cm of plot area (units cm$^{-2}$). Sampling was done after seven months of treatment and the samples were analyzed for thatch layer thickness, total organic carbon, and saturated hydraulic conductivity, acid-soluble lignin, and structural carbohydrates as described above. Two sub samples were collected from each plot for analysis. In addition, cultural management practice (core-aeration followed by top sand dressing) was used on certain plots, and compared its dethatching effects with laccase application.

First, these data clearly demonstrated the dethatching effect of laccase application in the field experiment, as evidenced by reduction in thatch layer thickness in all three grasses (FIG. 9). Further, these data suggest that the dethatching effect was accompanied with reduction of both lignin and carbohydrate contents in the thatch layer, as seen in FIG. 10 and FIG. 11. This is consistent with the notion that laccase activity decreases lignin content in plant cell walls to the point that it facilitates the microbial degradation of cellulose and hemicellulose.

Second, these data showed that dethatching effect was achieved with laccase application at a wide range of activity levels (FIG. 12) and frequency of laccase application (FIG. 13). While purified enzyme from Sigma was used in the majority of the experiment, two additional sources of laccase enzymes from China were also used on bentgrass to compare the effectiveness of laccase from different sources. Industrial laccase enzyme (CH I) and laccase from Jiangnan University (CH U) both proved effective in reducing thatch buildup (FIG. 12).

Third, these data demonstrated that laccase application in combination with cultural management practice, e.g., core-aeration followed by sand topdressing, lead to better dethatching effect than that of the cultural management practice alone (FIG. 14).

Example 5

Enzyme Immobilization to Topdressing

The present example describes preparation of a new enzyme delivery formulation. In this approach, laccase is first immobilized to sand surfaces by a method described below, and then the sand can be applied to turf as topdressing. This enzyme application approach can significantly reduce enzyme consumption because immobilized enzymes have greater stability and can stay in the top thatch layer for longer time with less mobility.

One protocol is schematically represented in FIG. 15. Briefly, the surface of the sands was first coated with polyethyleneimine followed by crosslinkage with gultaraldehyde to graft aldehyde groups onto the surface, and then enzymes were covalently bonded to the particles by formation of Schiff bases between the aldehyde groups and free amino groups on protein surface (Liu et al. 2005). The laccase immobilization appeared to be very effective.

In another exemplary protocol Laccase immobilization on sand is done in two phases. First, the sand is treated with chitosan and gluteraldehyde (two materials commercially available at low costs) to develop charges on the surface of sand. Second step will be enzyme loading and activity assessment. A two percent chitosan solution is prepared in 5% acetic acid. A 2 kg portion of sand is suspended in 5 L of this solution and mixed using a stirrer for one hour. After one hour, sand is collected and washed once with water. Sand is mixed with 3 L 10% gluteraldehyde solution and mixed for two hours. Sand is washed with water and dried overnight in an oven at 100±5° C. The next step is to load the sand with laccase enzyme at an optimized level to saturate the sand laccase carrying capacity that is determined via preliminary tests. The enzyme loading is done by treating the charged sand particles with laccase enzyme for two hours. Afterward, sand is washed with water and the activity of immobilized laccase is determined as mentioned above. Based on the measured activity, the amount of sand needed for each plot to achieve enzyme dosage comparable to other examples will be calculated and used in sand topdressing.

Yet another exemplary protocol involves the so-called layer-by-layer (LbL) assembly approach (Caruso and Schüler. 2000). The assembly involves alternate sorption of a polycation substrate, a polyanion substrate, or the enzyme onto the sands. Each sorption step is carried out in a separate solution with pH deliberately adjusted to render the substrates or the enzyme having appropriate charges. Each sorption step leads to a reversal of the terminal surface charge after adsorption of a new layer. One example of a conventional LbL method is described below. Poly (allylamine hydrochloride) (PAH) and poly(sodium 4-styrenesulfonate) (PSS) are used as the polyanions and polycations, respectively. Both chemicals are prepared at a concentration of 1 mg/mL in 0.05 M sodium acetate buffer at pH 4.5. The pH of the enzyme solution is carefully adjusted to several units away from their isoelectric points ($PI_{laccase}$=3.7), maintain a net negative or positive charge. Sequential polyelectrolyte/enzyme layers are deposited to form repetitive sand-PAH-PSS-enzyme or sand-PAH-PSS-PAH-enzyme sandwich assemblies. For each assembly step, the polyelectrolyte/enzyme is allowed to equilibrate with the sand particles for 20 min at room temperature under shaking condition.

Many variations and modifications may be made to the embodiments described in the preceding Examples. All such modifications and variations are intended to be included herein within the scope of this disclosure and protected by the following claims.

References

Baldrian, P. 2006. Fungal laccases-occurrence and properties. FEMS Microbiol Rev. 30: 215-242.

Barton, L., G. G. Y. Wan, R. P. Buck, and T. D. Colmer. 2009. Effectiveness of cultural thatch-mat controls for young and mature kikuyu turfgrass. Agron. J. 101: 67-74.

Beard, J. B. 1973. Turfgrass: Science and culture. Prentice Hall Inc. Englewood Cliffs, N.J.

Blanchette, R. A. 1984. Screening wood decayed by white rot fungi for preferential lignin degradation. Appl. Environ. Microbiol. 48: 647-653.

Boyle, C. D, B. R. Kropp and I. D. Reid. 1992. Solubilization and mineralization of lignin by white rot fungi. *Applied and Environmental Microbiology* 58 (3): 3217-3224.

Bunnell, B. T., L. B. McCarty, and H. S. Hill. 2001. Summer cultivation effects on sand based creeping bentgrass golf green. Int. Turfgrass Res. J. 9:3-9.

Callahan, L. L., W. L. Sanders, J. M. Parham, C. A. Harper, L. D. Lester, and E. R. McDonald. 1998. Cultural and chemical controls of thatch and their influence on rootzone nutrients in bentgrass green. Crop Sci. 38:181-187.

Carley, D. S., D. Goodman, S. Sermons, W. Shi, D. Bowman, G. Miller, and T. Rufty. 2011. Soil Organic matter accumulation in creeping bentgrass greens: A hronosequence with implications for management and carbon sequestration. Agron. J. 103 (3): 604-610.

Carrow, R. N. 2003. Surface organic matter in bentgrass greens. USGA Turfgrass Environ. Res. Online 2(17): 1-10.

Carrow, R. N. 2004. Surface organic matter in bentgrass greens. Golf Course Mgt. 72(5): 96-101.

Carrow, R. N., B. J. Johnson, and R. E. Burns. 1987. Thatch and quality of tifway bermudagrass turf in relation to fertility and cultivation. Agron. J. 79: 524-530.

Causo F., and C. Schuler. 2000. Enzyme multilayers on colloid particles: Assembly, stability, and enzymatic activity. Langmuir. 16: 9595-9603.

Chen, Y. R., and S. Sarkanen. 2003. Macromolecular lignin replication: A mechanistic working hypothesis. Phytochemistry Rev. 2: 235-255.

Couillard, A., A. J. Turgeon, and P. E. Rieke. 1997. New insights into thatch biodegradation. Int. Turfgrass Res. J. 8:427-435.

Davin, L. B. and N. G. Lewis 2003. A historical perspective on lignin biosynthesis: Monolignol, allyiphenol and hydroxycinnamic acid coupling and downstream metabolism. Phytochemistry Rev. 2: 257-288.

Dunn, J. H., K. M. Sheffer, and P. M. Halisky. 1981. Thatch and quality of Meyer zoysia in relation to management. Agron. J. 73: 949-952.

Eggens, J. L. 1980. Thatch control on creeping bentgrass turf. Can. J. Plant Sci. 60:1209-1213.

Engel, R. E. 1954. Thatch on turf and its control. Golf Course Rep. 22 (5): 12-14.

Engel, R. E., and R. B. Alderfer. 1967. The effect of cultivation, top-dressing, lime, N, and wetting agent on thatch development on ¼-inch bentgrass over a 10-year period. N.J. Agric. Exp. Stn. Bull. 818:32-45.

Gold, M. H. and M. Alic. 1993. Molecular biology of lignin-degrading basidiomycete *phanerochaete chryosporium*. Microbiology and Molecular biology reviews. 57(3): 605-622.

Hartwiger, C. 2004. The importance of organic matter dynamics: How research uncovered the primary cause of secondary problems. USGA Green Section Record 42(3): 9-11.

Johnson, B. J., R. N. Carrow, and R. E. Burns. 1987. Bermudagrass turf response to mowing practices and fertilizer. Agron. J. 79:677-680.

Kirk, T. K., and R. L. Farrell. 1987. Enzymatic "combustion": Theicrobial degradation of lignin. Annu. Rev. Microbiol. 41: 465-501.

Kirk, T. K., W. J. Connors, R. D. Bleam, and G. Jeikus. 1976. Requirements for a growth substrate during lignin decomposition by two wood-rotting fungi. Appl. Environ. Microbiol. 32: 192-194.

Kirk, T. K., W. J. Connors, R. D. Bleam, W. F. Hackett, and J. G. Jeikus. 1975. Preparation and microbial decomposition of synthetic [$^{14}$C] lignins. PANS. 72: 2515-2519.

Landreth, J., D. Karcher, and M. Richardson. 2008. Cultivating to manage organic matter in sand based putting greens: University of Arkansas researchers provide important insight for managing organic buildup on putting greens. USGA Turfgrass Environ. Res. Online 46(1): 16-19.

Ledeboer, F. B., and C. R. Skogley. 1967. Investigations into the nature of thatch and methods for its decomposition. Agron. J. 59: 320-323.

Liu Z. M., Liu Y. L., Yang H. F., Yang Y., Shen G. L., and R. Q. Yu. 2005. A phenol biosensor based on immobilizing tyrosinase to modified core-shell magnetic nanoparticles supported at a carbon paste electrode. Analytica Chimica Acta 533: 3-9.

Martin, S. B., and J. L. Dale. 1980. Biodegradation of turf thatch with wood-decay fungi. Phytopathology. 70: 297-301.

McCarty, L. B., M. F. Gregg, and J. E. Toler. 2007. Thatch and mat management in an established creeping bentgrass green. Agron. J. 99: 1530-1537.

McCarty, L. B. 2005. Best golf course management practices. 2$^{nd}$ ed. Prentice Hall Inc. Upper Saddle River, N.J.

McCarty, L. B., M. F. Gregg, J. E. Toler, J. J. Camberato, and H. S. Hill. 2005. Minimizing thatch and mat development in a newly seeded creeping bentgrass golf green. Crop Sci. 45:1529-1535.

McCoy, E. L. 1992. Quantitative physical assessment of organic materials used in sports turf rootzone mixes. Agron. J. 84: 375-381.

McWhirter, E. L., and C. Y. Ward. 1976. Effect of vertical mowing and aerification of golf green quality. Mississipi Agric. For. Exp. Stn. Res. Rep. 2 (12). 1-2.

Mester, T., E. Varela, and M. Tien. 2004. Wood degradation by brown-rot and white-rot fungi. The Mycota II: Genetics and biotechnology. 2$^{nd}$ edition. Springer-Verlag, Berlin, Heidelberg.

Munoz, C., F. Guillen, A. T. Martinez, and M. J. Martinez. 1997. Laccase isozymes of *Pleurotus* eryngii: Characterization, catalytic properties, and participation in activation of molecular oxygen and Mn$^{2+}$ oxidation. App. Environ. Microbiol. 63: 2166-2174.

Murdoch, C. L., and J. P. Barr. 1976. Ineffectiveness of commercial microorganism inoculums in breaking down thatch in common bermudagrass in Hawaii. HortScience. 11:488-489.

Murray, J. J., and F. V. Juska. 1977. Effect of management practices on thatch accumulation, turf quality, and leaf spot damage in common Kentucky bluegrass. Agron. J. 69: 365-369.

Nakayama T. and T. Amachi. 1999. Fungal peroxidases: its structure, function and application. *Journal of Molecular catalysisB: Enzymatic.* 6(3): 185-198.

National Renewable energy Laboratory (NREL). Chemical Analysis and Testing Laboratory Analytical Procedures: LAP (2008). NREL, Golden, Colo., USA.

O'Brien, P., and C. Hartwiger. 2003. Aeration and topdressing for the 21$^{st}$ century: Two old concepts are linked together to offer up-to-date recommendations. USGA Green Section Record 41(2): 1-7.

Otjen, L., and R. Blanchette. 1987. Assessment of 30 white rot basidiomycetes for selective lignin degradation. Holzforschung. 41: 343-349.

Otjen, L., and R. Blanchette. 1987. Assessment of 30 white rot basidiomycetes for selective lignin degradation. Holzforschung. 41: 343-349.

Park, J. W., J. Dec, J. E. Kim, and J. M. Bollag. 1999. Effect of humic constituents on the transformation of chlorinated phenols and anilines in the presence of oxidoreductive enzymes or birnessite. Environ. Sci. Tech. 33: 2028-2034.

Rieke, P. E. 1994. Sand topdressing: here are we going? Golf Course Mgt. 62:36-38.

Roberts, E. C., and E. J. Bredakis. 1960. What, why and how of turfgrass root development. Golf Course Rep. 28:13-24.

Roper, J. C., J. M. Sarkar, J. Dec, and J. M. Bollag. 2000. Enhanced enzymatic removal of chlorophenols in the presence of co-substrates. Water Res. 29:2720-2724.

SAS Institute Inc. 1994. The SAS system for windows. Release 9.2. SAS Inst., Cary, N.C.

Sartain, J. B., and B. G. Volk. Influence of selected white-rot fungi and topdressings on the composition of thatch components of four turfgrasses. Agron. J. 76: 359-362.

Smith, G. S. 1979. Nitrogen and cultivation influence on putting green thatch and soil. Agron. J. 71:680-684.

Smiley, R. W., M. Crawen Fowler, R. T. Kane, A. M. Petrovic, and R. A. White. 1985. Fungicide effects on thatch depth, thatch decomposition rate, and growth of Kentucky bluegrass. Agron. J. 77: 597-602.

Soper, D. Z., J. H. Dunn, D. D. Minner, and D. A. Sleper. 1988. Effects of clipping disposal, nitrogen, and growth retardants on thatch and tiller density in zoysiagrass. Crop Sci. 28: 325-328.

Stoilova, I., A. Krastanov, and V. Stanchev. 2010. Properties of crude laccase from *Trametes versicolor* produced by solid-substrate fermentation. Adv. Bioscience Biotech. 1: 208-215.

Thurston, C. F. 1994. The structure and function of fungal laccases. Microbiol. 140:19-16.

Weston, J. B., and J. H. Dunn. 1985. Thatch and quality of Meyer zoysia in response to mechanical cultivation and nitrogen fertilization. P. 449-458. In F. Lemaire (ed.) Proc. 5th Int. Turfgrass Res. Conf., Avignon, France. 1-5 Jul. 1985. Institut National de la Recherche Agronomique, Paris, France.

White, R. H., and R. Dickens. 1984. Thatch accumulation in bermudagrass as influenced by cultural practices. Agron. J. 76: 19-22.

Wong, D. W. S. 2009. Structure and action mechanism of ligninolytic enzymes. Appl. Biochem Biotechnol. 157: 174-209.

We claim:

1. A method of degrading turf thatch, comprising contacting the turf thatch with a composition comprising:
an isolated fungal laccase enzyme immobilized to particles of particulate topdressing.

2. The method of claim 1, wherein the laccase enzyme is from white rot fungi.

3. The method of claim 1, wherein the laccase enzyme is from *Trametes versicolor*.

4. The method of claim 1, wherein the composition further comprises a mediator.

5. The method of claim 4, wherein the mediator is chosen from the following: catechol, guaiacol, ABTS, and violuric acid.

6. The method of claim 5, wherein the mediator comprises guaiacol.

7. The method of claim 1, wherein the composition is applied to the turf thatch in an amount of about 0.1 to about 20 units/cm$^2$ of turf area.

8. The method of claim 1, wherein the composition is applied to the turf thatch in an amount of about 0.206 units/cm$^2$ or more of turf area.

9. The method of claim 1, wherein the composition is applied to turf thatch at intervals ranging from one application about every 56 weeks to about once a week.

10. A composition for reducing turf thatch comprising:
a particulate topdressing, and
an isolated fungal laccase enzyme, wherein the laccase enzyme is immobilized to particles of the particulate topdressing.

11. The composition of claim 10, wherein the topdressing is sand and wherein the isolated fungal laccase enzyme is immobilized to sand particles.

12. The composition of claim 10, wherein the laccase enzyme is immobilized to particles of the topdressing by a linking agent.

13. The composition of claim 12, wherein the linking agent is chosen from: glutaraldehyde, chitosan, and a combination thereof.

14. The composition of claim 13, wherein the linking agent is glutaraldehyde.

15. The composition of claim 14, wherein the glutaraldehyde is linked to the particle by polyethylenimine.

16. The composition of claim 10, wherein the isolated fungal laccase enzyme is immobilized to the particles of topdressing by alternating layers of a polycation layer, a polyanion layer, and an enzyme layer.

17. The composition of claim 16, wherein the polycation layer comprises poly(sodium 4-styrenesulfonate)(PSS) and the polyanion layer comprises Poly(allylamine hydrochloride)(PAH).

18. The composition of claim 10, wherein the fungal laccase enzyme is isolated from *Trametes versicolor*.

* * * * *